(12) United States Patent
Allmendinger

(10) Patent No.: US 8,029,656 B2
(45) Date of Patent: *Oct. 4, 2011

(54) SYSTEM, APPARATUS, AND METHOD FOR MEASURING AN ION CONCENTRATION OF A MEASURED FLUID

(75) Inventor: Klaus K. Allmendinger, San Juan Capistrano, CA (US)

(73) Assignee: EmiSense Technologies LLC, San Juan Capistrano, CA (US)

(*) Notice: Subject to any disclaimer, the term of this patent is extended or adjusted under 35 U.S.C. 154(b) by 1104 days.

This patent is subject to a terminal disclaimer.

(21) Appl. No.: 11/767,629

(22) Filed: Jun. 25, 2007

(65) Prior Publication Data

US 2007/0261475 A1 Nov. 15, 2007

Related U.S. Application Data

(60) Continuation-in-part of application No. 11/244,210, filed on Oct. 5, 2005, now Pat. No. 7,249,489, which is a division of application No. 10/699,182, filed on Nov. 1, 2003, now Pat. No. 6,978,655.

(60) Provisional application No. 60/942,781, filed on Jun. 8, 2007, provisional application No. 60/443,628, filed on Jan. 30, 2003.

(51) Int. Cl.
*G01N 27/02* (2006.01)
*G01R 27/02* (2006.01)
*G01N 27/419* (2006.01)

(52) U.S. Cl. ....... 204/424; 73/23.31; 73/31.05; 204/425

(58) Field of Classification Search .......... 204/424–429; 205/781, 783.5–785; 73/23.31, 23.32, 31.05
See application file for complete search history.

(56) References Cited

U.S. PATENT DOCUMENTS

| 4,226,692 | A | * | 10/1980 | Isenberg | 204/406 |
| 4,384,935 | A | * | 5/1983 | De Jong | 204/406 |
| 6,442,998 | B2 | * | 9/2002 | Kurokawa et al. | 73/31.05 |
| 2002/0046947 | A1 | * | 4/2002 | Lawless | 204/426 |

* cited by examiner

*Primary Examiner* — Jeffrey T Barton
*Assistant Examiner* — Jennifer Dieterle
(74) *Attorney, Agent, or Firm* — Jeffrey T. Holman

(57) ABSTRACT

An apparatus, system and method maximizes efficiency and accuracy of measuring an ion concentration of a measured fluid by varying a flow of ions within a measuring cell in accordance with an output signal of a sensor cell. The pump current through a pump cell is switched between a constant positive current and a constant negative current when upper and lower thresholds of the output signal are reached. The pulse width ratio of the square wave produced by the varying current is compared to a pulse width ratio function derived from a calibration procedure to determine the ion concentration of the measured fluid. In one embodiment, the functions of the pump cell and sensing cell are performed by a single electrochemical cell.

22 Claims, 13 Drawing Sheets

FIG. 10    1000

SYSTEM, APPARATUS, AND METHOD FOR MEASURING AN ION CONCENTRATION OF A MEASURED FLUID

RELATED APPLICATIONS

This application is a continuation-in-part (CIP) patent application of a U.S. patent application Ser. No. 11/244,210 entitled "System, Apparatus, And Method For Measuring An Oxygen Concentration Of A Gas" filed on Oct. 05, 2005, now U.S. Pat. No. 7,249,489 which is a divisional patent application of U.S. patent application Ser. No. 10/699,182, filed on Nov. 01, 2003 now U.S. Pat. No. 6,978,655, entitled "System, Apparatus, And Method For Measuring An Oxygen Concentration Of A Gas" which claims the benefit of priority of U.S. Provisional Application Ser. No. 60/443,628 filed on Jan. 30, 2003, entitled "System, Apparatus, And Method For Measuring An Oxygen Concentration Of A Gas", all hereby incorporated by reference in their entirety herein. This application also claims the benefit of priority of U.S. provisional application Ser. No. 60/942,781, entitled "Pulse Width Modulation Wideband Ion Sensor", filed Jun. 08, 2007 and incorporated by reference in its entirety herein.

BACKGROUND

The invention relates in general to ion sensors and more specifically to an apparatus, system and method for monitoring an ion concentration of a measured fluid.

Wideband ion sensors are used to measure the concentration of particular ions within a fluid where the fluid may be a gas or liquid. A popular use of wideband gas ion sensors includes using oxygen sensors to determine on oxygen concentration within a gas mixture. Other examples of gas ion sensors include nitrogen sensors that sense gaseous oxides of nitrogen. Many conventional combustion engines utilize oxygen sensors for determining the air to fuel mixture of the exhaust of the combustion engine. Conventional internal combustion engines typically incorporate electronic fueling control using computing devices, such as Electronic Control Units (ECU), that meter fuel into the engine intake depending on engine intake airflow. Typically, the volume of fuel is regulated such that emissions are minimized and all of the fuel is completely burned. The theoretical ratio of air to fuel for complete combustion is 14.7 by weight for gasoline, called the stoichiometric ratio. Theoretically, all available fuel combines with all the intake air at the stoichiometric ratio. The unit Lambda ($\lambda$) is often used to represent the quotient of actual air to fuel ratio over the region near the stoichiometric ratio. Conventional electronic fueling systems typically include an oxygen sensor in the exhaust that measures the oxygen concentration of the exhaust. These oxygen sensors act as fuel cells that create an output voltage by combining unburned hydrocarbons in the exhaust with atmospheric oxygen. This results in a lambda/output transfer curve where a $\lambda$ of 1.0 corresponds to an output voltage of 0.45V. Using the oxygen sensor, the fueling control system regulates the fueling such that the resulting lambda is 1.0 at medium load conditions using a feedback loop. The transfer curve of a typical oxygen sensor is very steep where $\lambda$ is equal to 1.0, however, and significant variations in output voltage occurs for slight variations in $\lambda$. Accordingly, the measured voltage cannot be used to measure other $\lambda$ values. At high load conditions, a typical internal combustion engine produces maximum power at lambda values<one (0.75 to 0.85). Conventional ECU systems operate in an 'open loop' mode under these conditions where the volume of injected fuel is derived solely from pre-stored maps that relate intake air mass to fuel mass without feedback. Because engine aging and production variations change the actual air fuel ratio of the engine, these pre-stored conditions are not always correct for the particular engine. As a result, conventional systems are limited in that severe inefficiencies can occur at high load conditions. Many other wideband ions sensors experience similar drawbacks.

Some recent developments in engine technology have resulted in 'lean-burn' systems that operate at lambda ratios greater than 1 (up to 1.1) to minimize fuel consumption and further minimize emissions using special catalysators. Because ordinary lambda sensors are not usable in these lambda regimens, a 'wide-band' or Universal Exhaust Gas Oxygen (UEGO) sensor has been developed. UEGO sensors combine a small measurement chamber having an orifice open to the exhaust stream, a standard oxygen sensor (Nernst cell), and a pump cell. The pump cell is a solid-state device of porous ceramic that allows oxygen to move between the atmosphere and the measurement chamber. The direction and magnitude of the current through the pump cell (often referred to as the pump current) determines the direction and flow rate of oxygen ions. In conventional systems, an active feedback loop is incorporated such that the voltage at the oxygen sensor portion of the device is held at the stoichiometric voltage. The pump current can then be used to determine the $\lambda$ value over a wide range of ratios up to the ratio for free air.

FIG. 1 is graphical illustration of a typical relationship between the pump current and Lambda ($\lambda$). As shown in FIG. 1, the resulting curve of pump current vs. lambda value ($\lambda$) is non-linear. Although the curve shape does not vary, manufacturing tolerances in the sensors result in different magnitudes of pump current vs. lambda ($\lambda$) (i.e. the curve shifts). Attempts to compensate for the variations include incorporating a calibration resistor in the connector to the measuring cell sensor. Unfortunately, this attempted solution does not address all of the variations. Barometric air pressure and exhaust pressure also influence the lambda/pump current relationship. Accordingly, the outputs of theses sensors are not accurate. It is therefore desirable to have a measurement method for oxygen sensors that is self-calibrating and self-compensating for all the above variations.

The pump current vs. lambda curve is also highly temperature dependent. Typical UEGOs contain a heater element that maintains the sensor at the desired operating temperature. The temperature coefficient of the heater element is the quotient of change in resistance ($\Delta R$) to the change in temperature ($\Delta T$). Conventional techniques use the positive temperature coefficient of the heater element to regulate input by operating the element at a constant voltage. Because the temperature coefficient, $\Delta R/\Delta T$, is fairly small at the operating temperature, the resulting temperature regulation is not very precise. Depending on the sensor, the pump cell impedance, the Nernst cell impedance, or both have a much bigger temperature coefficient, $\Delta R/\Delta T$, and would, therefore, allow more precise temperature control. It would be more advantageous to control the temperature of the pump cell. Unfortunately, at lambda values near 1, the pump current is very small or equal to zero and the pump cell impedance can not be accurately measured on a low current. The Nernst cell is typically physically bonded to the pump cell and, therefore, the temperature of the Nernst cell and the pump cell differ by a small amount. In order to measure the Nernst cell impedance, a known fixed current or known fixed voltage have to be impressed on the Nernst cell and the resulting voltage or current then measured. Alternatively, a small alternating current (AC) voltage or current can be impressed on the Nernst cell and the resulting AC impedance measured. The first method requires stopping the lambda measurement for a period of time and also requires impressing the reverse charge on the Nernst cell to speed up recovery. The second method does not interfere with the measurement but requires low pass filters to remove the AC voltage or current from the measured signal. The filters also remove the higher signal frequencies which results in an inability to detect short transient responses. Both methods measure the temperature of the Nernst cell, not the pump cell. During operation, a temperature gradient between the pump cell and the Nernst cell may occur and some temperature control errors may result. Therefore there is a need for precise pump cell temperature control while measuring lambda without resorting to complicated circuitry to remove measurement artifacts.

Further, conventional fuel metering techniques result in significant pollution during the warm up period of the oxygen sensor. In conventional systems where UEGO sensors are used, a precise operating temperature must be attained before the UEGO output value is reliable. This increases the time the fuel injection systems runs in 'open loop' without knowledge of actual air-fuel ratio. As a result, the time the engine creates uncontrolled warm-up pollution is dependent on the sensor warm-up time. Therefore, there also exists a need for an apparatus, system and method for measuring an oxygen concentration which minimizes the time before a reliable value is produced by the sensor.

Current wideband ion sensors such as wideband oxygen sensors (WBO2 sensors) combine a Nernst cell reference sensor and a pump cell in single package. A Nernst cell is an electrochemical cell that produces a voltage that is nonlinearly proportional to the difference in partial pressure of a measured gas between electrodes of the cell. In a typical oxygen sensor application, the electrodes are exposed to atmospheric air on an electrode on one side of a measuring chamber and to an exhaust gas of an internal combustion engine on the other electrode. A voltage is created by oxygen ions migrating through the solid electrolyte material of the cell. The pump cell is a Nernst cell where oxygen ion flow through the cell is forced by an electrical current. If the current flows in one direction, oxygen ions are transported from the outside air into the sensor. If the current is reversed to the other direction, oxygen ions are transported out of the sensor to the outside air. The magnitude of the current determines the number of oxygen ions that are transported each second.

The Nernst voltage is a voltage created as result of electrochemical reaction in the cell. The cell acts basically as a fuel cell. The Nernst voltage is created by the difference in oxygen partial pressure between the two electrodes of the cell. The Nernst equation describes it:

$$V\text{output} = (R^*)(T)/(n)(F) * \ln[(Po,\text{air})/(Po,\text{exh})]$$

where,

Voutput=O2 sensor's output voltage (0 to 1.0 volt is a typical range)

$R^*$=Universal Gas Constant=8.3143 [Joule/gram-mole*K]

T=Temperature of the exhaust gas [Deg K]

n=number of electrons involved in the reaction=4 in the NBO2 case

F=Faraday constant=96,480 [Coulomb/gram-mole]

Po, air=Partial pressure of O2 in the atmosphere [Pascals]

Po, exh=Partial pressure of O2 in the exhaust gas at temp [Pascals].

In conventional systems, both the Nernst cell and the pump cell are mounted in a very small measurement chamber open with an orifice (diffusion gap) to the exhaust gas. During a rich condition, there is little or no oxygen and relatively high levels of oxidizable combustion products within the measuring chamber. In rich conditions, the WBO2 controller regulates the pump cell current such that just enough oxygen ions are pumped into the chamber to consume all oxidizable combustion products. This action basically produces a stoichiometric condition in the measurement chamber. In the stoichiometric condition, the Nernst reference cell produces 0.45V. In a lean condition where there is excess oxygen, the controller reverses the pump current so that all oxygen ions are pumped out of the measurement chamber and a stoichiometric condition returns. The pump cell is strong enough to pump all oxygen out of the measurement chamber even if the chamber is filled with free air.

The task of the WB controller in conventional systems, therefore, is to regulate the pump current such that there is never any oxygen nor oxidizable combustion products in the measurement chamber. The required pump current is a measure of the Air/Fuel ratio. Conventional wideband sensors, however, are difficult to produce because multiple cells are combined in a small package. Also, the small orifice to exhaust gas is susceptible to contamination or blockage by exhaust particles limiting performance of the sensor. In addition, conventional wideband sensors exhibit a delay between Nernst reference cell output and changing pump cell current because of the physical separation between the two devices. Accordingly, an improved ion sensor is needed.

DETAILED DESCRIPTION

As explained above, conventional sensor systems are limited in several ways. These limitations are overcome in the exemplary embodiment which provides an efficient, low cost, accurate method for measuring an ion concentration of fluid. An ion concentration of a fluid is measured by varying a pump current through a measuring cell based on an output of the measuring cell and observing the pulse width ratio of the resulting square wave representing the pump current. Further, in some circumstances, the method described herein allows the sensor to be used earlier in the warm-up period because the measurement method allows the application of a correction factor that compensates for the fact that the sensor has not yet achieved its desired operating temperature. Also, the exemplary embodiment described herein allows precise pump cell temperature control while measuring lambda without resorting to complicated circuitry to remove measurement artifacts. In addition to determining oxygen ion concentrations, the exemplary embodiment can be used to determine other gas ion concentrations. For example, nitrogen sensors such as sensors that sense gaseous oxides of nitrogen (NOx) can be connected to a current managing device and a computer device to measure ion concentrations of gaseous oxides of nitrogen such as NO and $NO_2$ ion levels. In a second exemplary embodiment, a single device performs the functions of the pump cell and the sensor cell.

Figure 1:
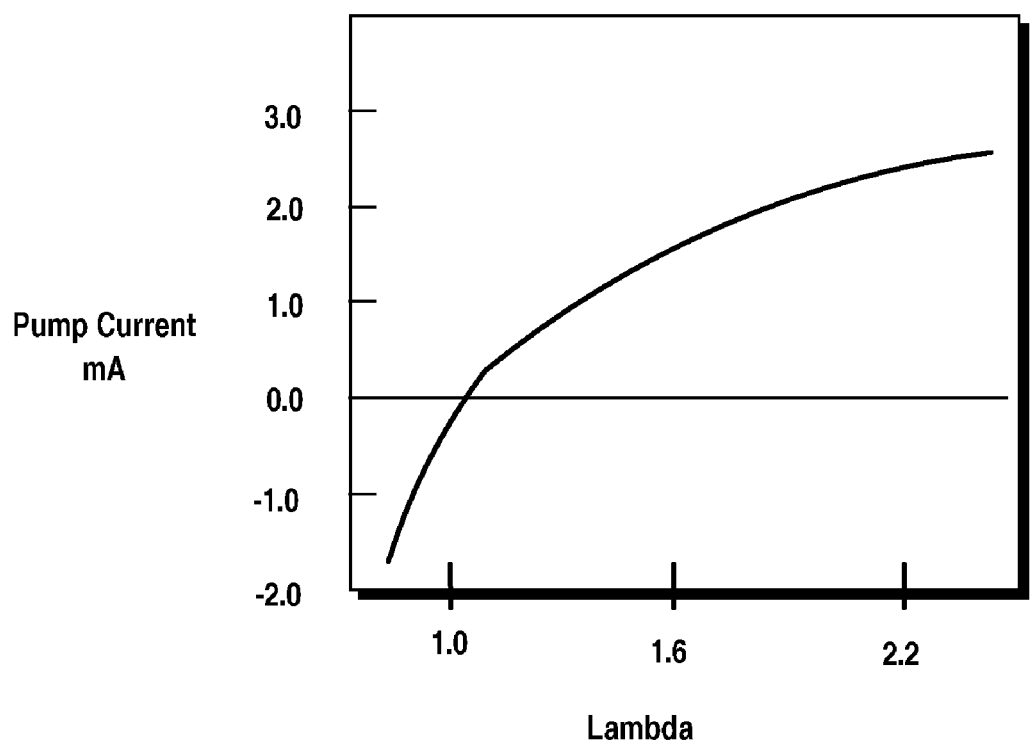
FIG. 1 is graphical representation of a relationship between pump current and an air to fuel ratio, Lambda (λ), for a typical Universal Exhaust Gas Oxygen (UEGO) sensor.
Figure 2A:
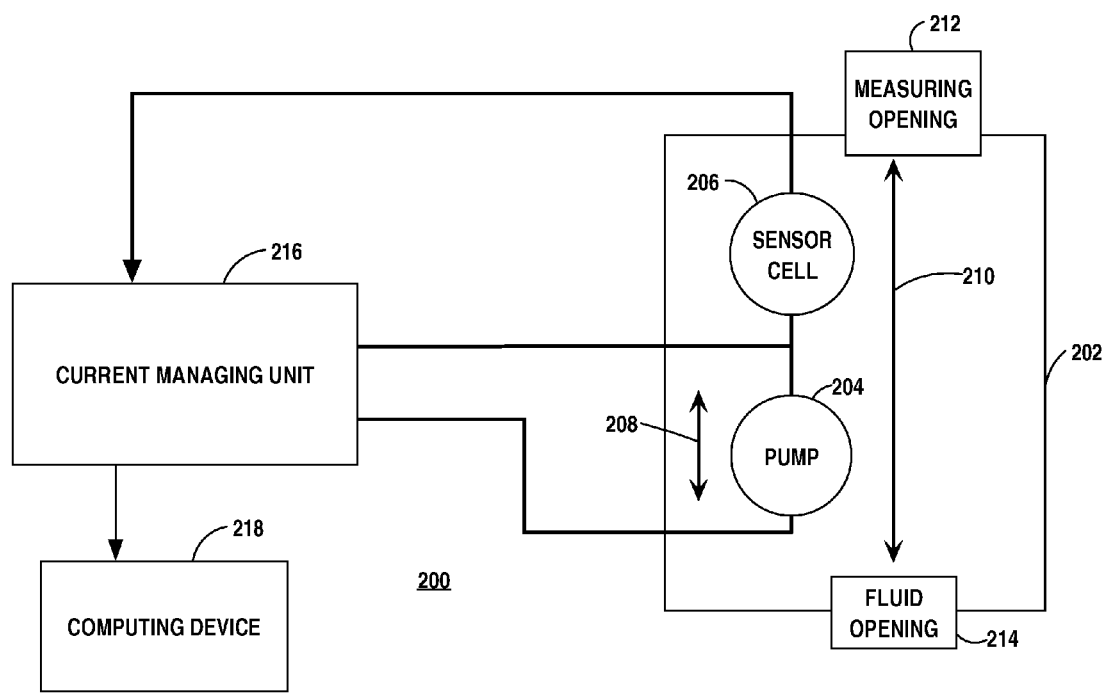
FIG. 2A is a block diagram of the oxygen monitoring device in accordance with an exemplary embodiment of the invention.

FIG. 2A is a block diagram of the ion monitoring device 200 in accordance with an exemplary embodiment of the invention. The ion monitoring device 200 may be implemented using any combination of hardware, software and firmware. Various functions and operations of the functional blocks described herein may be implemented in any number of devices, circuits or elements. Any of the functional blocks may be integrated in a single device and the functions of the blocks may be distributed over several devices, circuits and elements.

A measuring cell 202 includes at least a pump cell 204 and an ion sensor cell 206 where a magnitude and direction of a pump current 208 through the pump cell 204 is correlated to a flow of ions 210 within the measuring cell 202. A measuring opening 212 of the measuring cell 202 is positioned to receive a measured fluid while a fluid opening 214 faces an ambient fluid. The measured fluid and ambient fluid may be a gases or liquids. As discussed below, for example, the measured fluid is a measured gas and the ambient fluid is ambient air. The ion sensor cell 206 provides an output signal based on the number of ions within the measuring cell 202. In response to the output signal, a current managing unit 216 varies the pump current between two constant current levels. A first pump current is maintained by the current managing unit 216 until the output signal reaches a first threshold. When the first threshold is reached, the current managing unit 216 directs the pump current 208 in the opposite direction until the output signal reaches a second threshold level. A computing device 218 monitors the current fluctuation to determine an ion concentration of the measured fluid. As discussed below, a suitable application of the ion monitoring device 200 includes a gas ion monitoring device for monitoring exhaust gas from a combustion engine to determine oxygen concentrations for adjusting an air-fuel mixture. The ion monitoring device, method, and system may be implemented as part of any of several types of applications and systems and may be used to measure any of numerous types of ions within a fluid medium. Some examples include measuring ion concentrations of gaseous oxides of nitrogen such as NO and $NO_2$ ion levels, measuring carbon dioxide levels, measuring gas ion concentrations in liquids such as oxygen and carbon dioxide concentrations in water. Further, ion concentrations of salts and elements such as lead within liquids or gases may be measured in some situations. Accordingly, any of numerous types of ion concentrations may be measured where the ion sensor and current pump are responsive to the particular ions that are measured.

After a calibration procedure is performed, the current managing unit 216 varies the current 208 through the pump cell 204 between a constant positive current (Ip) and a constant negative current (–Ip) based on the output signal of the ion measuring cell 206. When a negative current (–Ip) flows through the pump cell 204, ambient fluid is received through the fluid opening 214 into the measuring cell 202 through the pump circuit which results in an increase of the ion concentration within the measuring cell 202. At a high ion concentration of oxygen within the measuring cell 202, the ion measuring cell 206 provides a low voltage signal output. When an output signal lower threshold is reached, the current managing unit 216, directs a positive current (Ip) through the pump cell 204. When a positive current (Ip) flows through the pump cell 204, the ions in the measuring cell 202 flow out to the ambient fluid. As the positive pump current 208 (Ip) continues to flow, ions continue to flow out of the fluid opening 214. As a result, the ion concentration continues to decrease. The output signal continues to increase until an upper threshold is reached. In response to detecting that the upper threshold has been reached, the current managing unit 216 changes the direction of the pump current 208. Exampled of suitable values for the threshold include values that maintain the ion measuring sensor 206 within a linear range or substantially linear range.

A square wave is formed between the positive and negative current levels. The duration of the pump current 208 at positive flow (Ip) and negative flow (–Ip) depends on the composition of the measured fluid. Accordingly, the computing device 218 compares the pulse width ratio ($PWM_{RATIO}$) of the resulting square wave to a known pulse width ratio function to determine the ion concentration of the measured fluid.

Figure 2B:
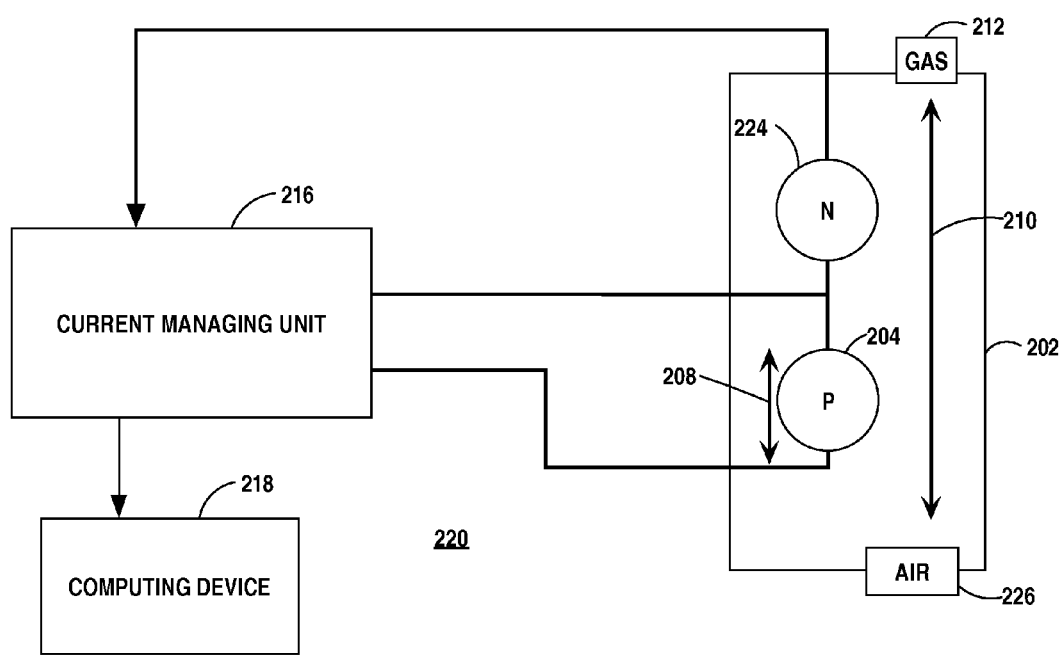
FIG. 2B is a block diagram of an exemplary ion monitoring device where the ion measuring device is a gas ion measuring device configured to measure an oxygen ion concentration within a measured gas.

FIG. 2B is a block diagram of an exemplary ion monitoring device 200 where the ion measuring device is a gas ion measuring device configured to measure oxygen ion concentration within a measured gas. The oxygen monitoring device 222 may be implemented using any combination of hardware, software and firmware. Various functions and operations of the functional blocks described herein may be implemented in any number of devices, circuits or elements. Any of the functional blocks may be integrated in a single device and the functions of the blocks may be distributed over several devices, circuits and elements.

In the exemplary oxygen monitoring device 222, the pump cell 204 and the ion measuring cell 206 are responsive to oxygen ions. The ion measuring cell 206 is an oxygen measuring cell 224. The measuring cell 202 in the oxygen monitoring device 222, therefore, includes at least the pump cell 204 and an oxygen sensor cell 224 where a magnitude and direction of a pump current 208 through the pump cell 204 is correlated to a flow of oxygen ions 210 within the measuring cell 202. The measuring opening 212 of the measuring cell 202 is positioned to receive a measured gas while the fluid opening 214 is an air opening 226 that faces ambient air. The oxygen sensor cell 224 provides an output signal based on the number of oxygen ions within the measuring cell 202. In response to the output signal, the current managing unit 216 varies the pump current between two constant current levels. A first pump current is maintained by the current managing unit 216 until the output signal reaches a first threshold. When the first threshold is reached, the current managing unit 216 directs the pump current 208 in the opposite direction until the output signal reaches a second threshold level. The computing device 218 monitors the current fluctuation to determine an oxygen concentration of the measured gas. A suitable application of the oxygen monitoring device 222 includes monitoring exhaust gas from a combustion engine to determine oxygen concentrations for adjusting an air-fuel mixture. The oxygen monitoring device, method, and system may be implemented as part of any of several types of applications and systems. As discussed below, for example, the oxygen monitoring device 222 may be implemented as a hand-held diagnostic device, as an original equipment manufacturer (OEM) device within a vehicle, or as an aftermarket device for permanent installation in a vehicle. In addition to measuring oxygen, the exemplary oxygen measuring device and method may be used to measure the oxygen concentration of exhaled gases from a living being to determine the number of calories that are being expended. Accordingly, the device and method discussed with reference to FIG. 2B is only one example of the numerous applications of the measuring system.

In the exemplary embodiment, the oxygen sensor cell 224 is a Nernst cell (224) that is positioned adjacent to a pump cell 204 in accordance with known techniques. Other types of oxygen sensor cells 224 may be used, however. It is understood by those skilled in the art that although the following description refers to a Nernst cell (224), the invention may be implemented with other oxygen sensor cells 224 capable of providing an output signal based on the oxygen level in a measured gas. After a calibration procedure is performed in accordance with the procedure described below, the current managing unit 216 varies the current 208 through the pump cell 204 between a constant positive current (Ip) and a constant negative current (−Ip) based on the output signal of the Nernst cell (224). When a negative current (−Ip) flows through the pump cell 204, ambient air is received through the air opening 226 into the measuring cell 202 through the pump circuit which results in an increase of the concentration of oxygen within the measuring cell 202. At a high concentration of oxygen within the measuring cell 202, the Nernst cell (224) provides a low voltage signal output. When an output signal lower threshold is reached, the current managing unit 216, directs a positive current (Ip) through the pump cell 204. When a positive current (Ip) flows through the pump cell 204, the oxygen ions in the measuring cell 202 flow out to ambient air. Any unburned carbons or fuel within the measuring cell 202 combine with any remaining oxygen. As a result, the mixture of air and unburned carbons within the measuring cell 202 decreases in oxygen concentration and increases in fuel concentration. The output signal increases through the transition point where no unburned fuel and no excess oxygen is present in the measuring cell 202. At this transition point, lambda is equal to 1.0 and the Nernst cell (224) provides an output signal of approximately 450 mV. As the positive pump current 208 (Ip) continues to flow, oxygen ions continue to flow out of the air opening 214. As a result, the concentration of oxygen continues to decrease and the concentration of fuel increases in the measuring cell 202. The output signal continues to increase until an upper threshold is reached. In response to detecting that the upper threshold has been reached, the current managing unit 216 changes the direction of the pump current 208. In the exemplary embodiment, the upper threshold is 455 mV and the lower threshold is 445 mV. Other thresholds, however, can be used where some suitable values include values providing a range that includes the output signal for gas of ambient air and which maintain the Nernst cell (224) within a relatively linear potion of the lambda to voltage relationship. For example, another suitable pair of values includes 440 mV and 460 mV.

As discussed above, a square wave is formed between the positive and negative current levels. The duration of the pump current 208 at positive flow (Ip) and negative flow (−Ip) depends on the composition of the measured gas. Accordingly, the computing device 218 compares the pulse width ratio ($PWM_{RATIO}$) of the resulting square wave to a known pulse width ratio function to determine the oxygen concentration of the measured gas.

Figure 3:
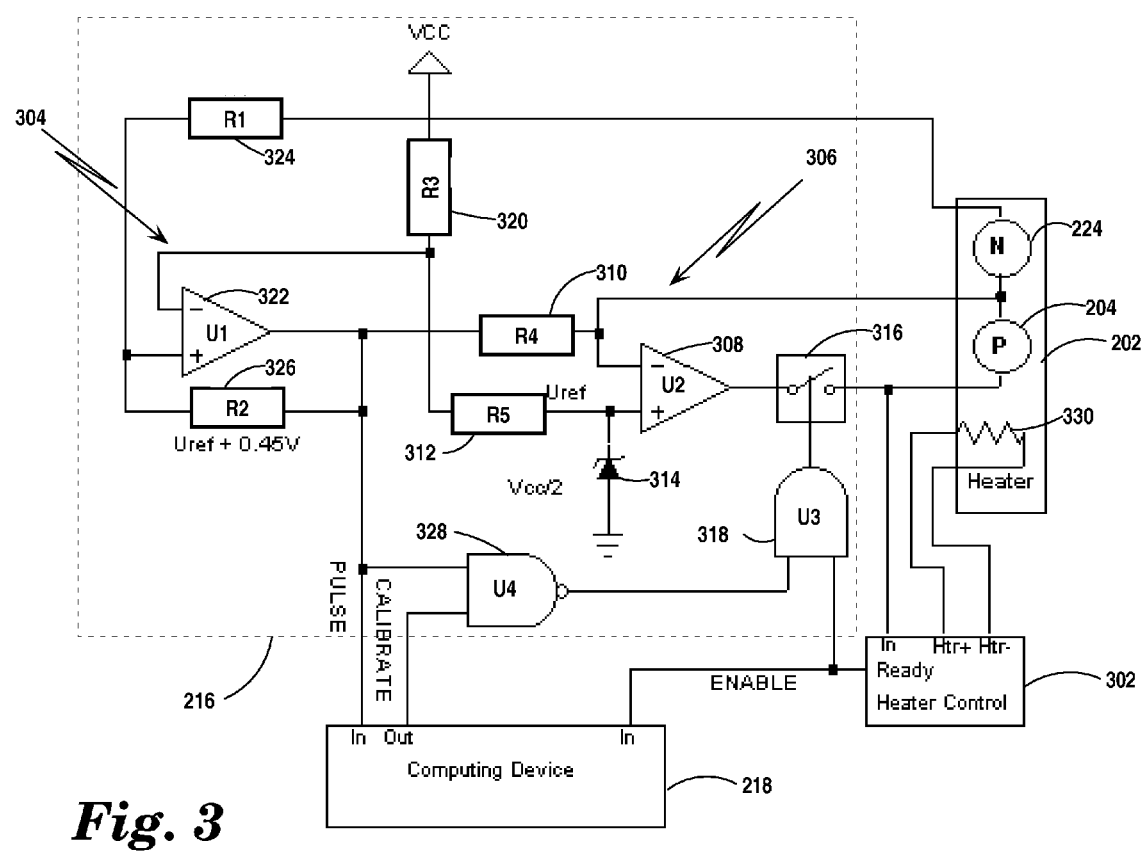
FIG. 3 is a schematic representation of the oxygen monitoring device where the current managing unit is implemented using an analog comparator circuit and an inverting amplifier circuit in accordance with the exemplary embodiment of the invention.

FIG. 3 is a schematic representation of the oxygen monitoring device 222 where the current managing unit 216 is implemented using an analog comparator circuit 304 and an inverting amplifier circuit 306 in accordance with the exemplary embodiment of the invention. The current managing device 216 may be implemented using any combination and arrangement of hardware, software and firmware. In the exemplary embodiment, the current managing device 216 includes several hardware components including resistors, operational amplifiers, analog switches, Zener diodes, logic gates and other circuits. Those skilled in the art will recognize the various substitutions that can be made for one or more circuits or circuit elements by applying the teachings herein in accordance with known techniques. Further, the operating values may differ depending on the particular implementation of the current managing device 216. Although the discussion with reference to FIG. 3 is directed to oxygen sensors, the teachings can be applied to other types of wideband sensors.

The inverting amplifier circuit 306 at least includes an operational amplifier ($U_2$) 308, an inverting input resistor ($R_4$) 310, and a non-inverting input resistor ($R_5$) 312. The voltage at the non-inverting input of the operational amplifier ($U_2$) 308 is maintained at voltage of $U_{REF}$ by a Zener diode 314. $U_{REF}$ is equal to Vcc/2 which is approximately 2.5 volts in the exemplary embodiment. The pump cell 204 in the measuring cell 202 is connected through an analog switch 316 between the output of the operational amplifier ($U_2$) 308 and the inverting input of the operational amplifier ($U_2$). The operational amplifier ($U_2$) 308, inverting input resistor ($R_4$) 310 and the pump cell 204 impedance ($R_{pump}$) form the inverting amplifier 306 with a gain of $-R_{pump}/R_4$. The output of the operational amplifier ($U_2$) 308 is connected to the analog switch 316 that connects the output of the operational amplifier 308 to the pump cell 204 in response to the output level of an AND gate ($U_3$) 318. Since the AND gate 318 provides an active "high" output when the heater control unit 302 presents a "high" enable signal, the analog switch 316 prevents current from flowing through measuring cell 202 during warm up. Further, as explained below, during the calibrate procedure, the analog switch 316 is opened during the negative pump current 208 cycle resulting in a pump current 208 that alternates between a positive pump current (IP) and zero.

The inverting input of the operational amplifier ($U_2$) 308 is connected to the output of the analog comparator circuit 304 through the inverting input resistor ($R_4$) 310. The non-inverting input resistor ($R_5$) 312, a supply resistor ($R_3$) 320 and the Zener diode 314 form a voltage divider and present a reference voltage of (Vcc/2+0.45V) to the inverting input of an operational amplifier ($U_1$) 322 of the analog comparator circuit 304. In the exemplary embodiment, the reference voltage is 2.95 Volts since Vcc is 5 Volts. The positive input of the operational amplifier 322 is connected to the output of the Nernst cell (224) through a sensing resistor ($R_1$) 324. A feedback resistor ($R_2$) 326 provides a voltage equal to $U_{REF}$+ 0.45V to the positive input of the operational amplifier 322. Therefore, the operational amplifier ($U_1$) 322, the resistor ($R_1$) 324, and the feedback resistor ($R_2$) 326 form the analog comparator circuit 304 operating with a hysteresis voltage of approximately 10 mV.

The analog comparator circuit 304, the inverting amplifier circuit 306 and the measuring cell 202 form an oscillator with a variable pulse width modulation (PWM) ratio and a frequency that is dependent on the response time of the measuring cell 202. The pump current 208 alternates between +Vcc/(2*R4) and −Vcc/(2*R4). The computing device 218 measures the times the output of U2 spends above ($t_1$) and below Vcc/2 ($t_2$) and from that calculates the $PWM_{RATIO}$ and λ according to the function described below. Lambda (λ) is calculated at every transition of the output of the comparator in the exemplary embodiment. The Nernst cell (224) provides an output signal approximately between 0.1 V and 0.7 V and the resulting (λ) measurement frequency is about 7 octaves higher than the 3 dB point of the response frequency of the oxygen sensor cell 206. Accordingly, the oxygen sensor cell 224 response frequency is well above the Nyquist frequency in the exemplary embodiment.

In the exemplary embodiment, the heater control unit 302 increases the temperature of the measuring cell 202 using a sensor specific method and ramp-up schedule. After the measuring cell 202 has achieved its operating temperature, the "Ready" output of the heater control unit 302 goes active providing a high ENABLE signal to the AND gate ($U_3$) which closes the analog switch 304. The enable signal is also connected to an input of the computing device 218 and indicates to the computing device 218 that the measuring cell 202 is ready for operation. The heater control unit 302 then maintains a constant predetermined voltage over the heater element or uses other (sensor specific) methods for temperature regulation. In the exemplary embodiment, the pump cell impedance is measured when the heater element 330 impedance is at the minimum value. The pump cell impedance is maintained at the measured value by continually monitoring the pump cell impedance and adjusting the temperature with the heater element 330.

As described below with reference to FIG. 6, the computing device 218 stores values in non-volatile memory corresponding to the PWM ratio at the stoichiometric ratio (PWMST) and the pulse width ratio for air (PWMAIR). In the exemplary method described below with reference to FIGS. 4-8, a nominal lambda value having an error on the order of +/−5% is calculated based on the calibration values and the measured PWMRATIO. Because PWMST is dependent on the characteristics and age of the sensor much more than on environmental conditions, the calibration process does not need to be performed very often in most circumstances.

Based on these teachings, those skilled in the art will recognize the various components, devices, and circuits elements that can be used in the measuring device. An example of suitable device that can be used for the operational amplifiers 308, 322 include the TLV2463 operational amplifier available from the Texas Instruments company. Values for the inverting resistor ($R_4$) 310 and the non-inverting ($R_5$) resistor 312 are on the order of a few hundred ohms. An example of suitable computing device 218 includes an 850 Family RISC 8-Bit Microcontroller. In some circumstances, some or all of the functional blocks described above may be implemented as an application specific integrated circuit (ASIC). For example, heater control and current managing unit 216 and computing device 218 can be easily integrated into a mixed signal ASIC with very few external parts.

Figure 4:
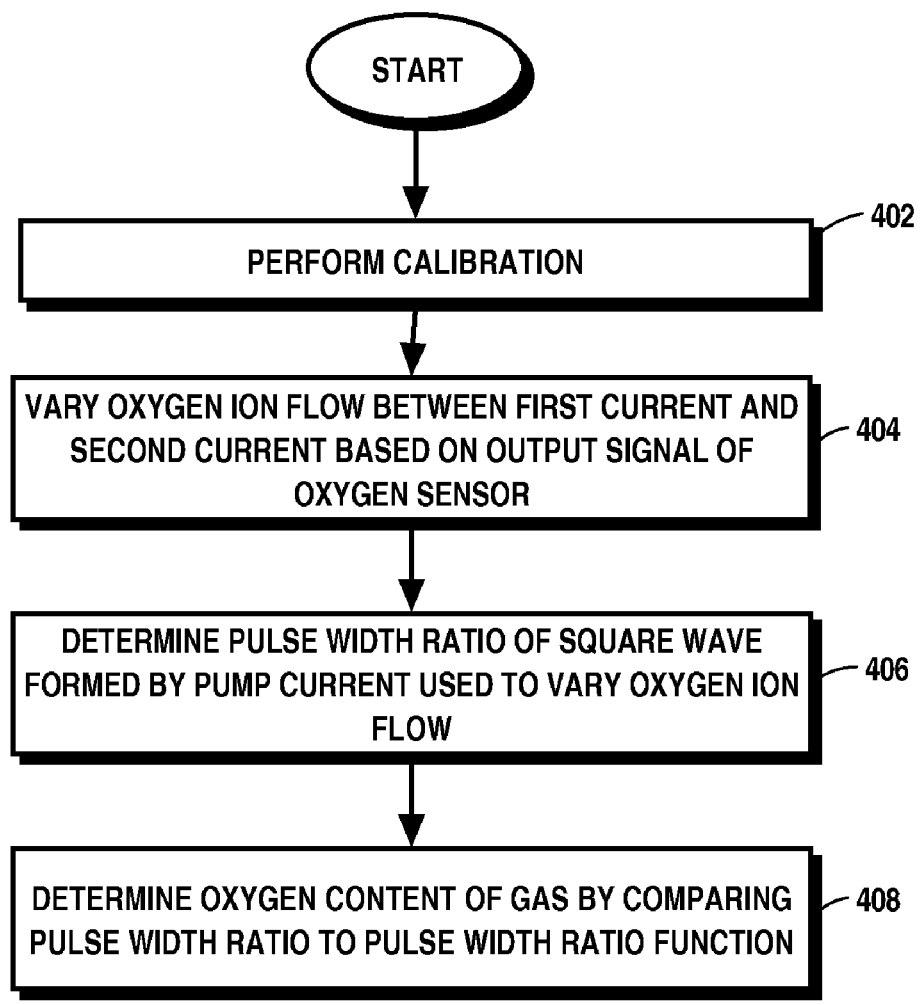
FIG. 4 is a flow chart of a method of measuring an oxygen concentration of a gas in accordance with the exemplary embodiment of the invention.

FIG. 4 is a flow chart of a method of measuring an oxygen concentration of a gas in accordance with the exemplary embodiment of the invention. The method may be performed with any combination of hardware, software or firmware. In the exemplary embodiment, the method is performed in the oxygen measuring device 222. Although the discussion with reference to FIG. 4 is directed to oxygen sensors, the teachings can be applied to other types of wideband sensors.

At step 402, a calibration procedure is performed. The calibration procedure obtains the calibration values for initializing the oxygen measuring device and may include values related to the characteristics of the particular measuring cell 202 or related to environmental conditions. As explained below with reference to FIG. 6, in the exemplary embodiment, values are obtained for maintaining the pump cell 204 impedance, for establishing the pulse width ratio function for calculating lambda, and for adjusting the lambda value when the PWM ratio for a stoichiometric ratio ($PWM_{ST}$) is not zero. Other calibration values may include parameters related to the frequency of a square wave of the pump current 208 reflecting oxygen sensor characteristics.

At step 404, the oxygen ion flow is varied between a first pump current and a second pump current based on the output signal of the oxygen sensor cell 224. In the exemplary embodiment, the ion flow is varied by alternating the pump current 208 between a positive constant current (IP+) and a negative constant current (IP−). The analog switch 316 remains closed during the measurement procedure.

At step 406, the pulse width ratio ($PWM_{RATIO}$) of the square wave formed by the pump current 208 is determined by the computing device 218. In the exemplary embodiment, the pulse widths ($t_1$ and $t_2$) of the square wave formed by the varying pump current 208 are measured using a crystal clock in the computing device 218. Although individual values of a single pulse can be measured and stored, the duration of the pulses resulting form the varying current are averaged over a time period.

At step 408, the pulse width ratio ($PWM_{RATIO}$) is compared to the pulse width ratio function to determine the oxygen concentration of the measured gas. In the exemplary embodiment, the computing device 218 applies the measured values to equations that utilize the calibrated values.

Figure 5:
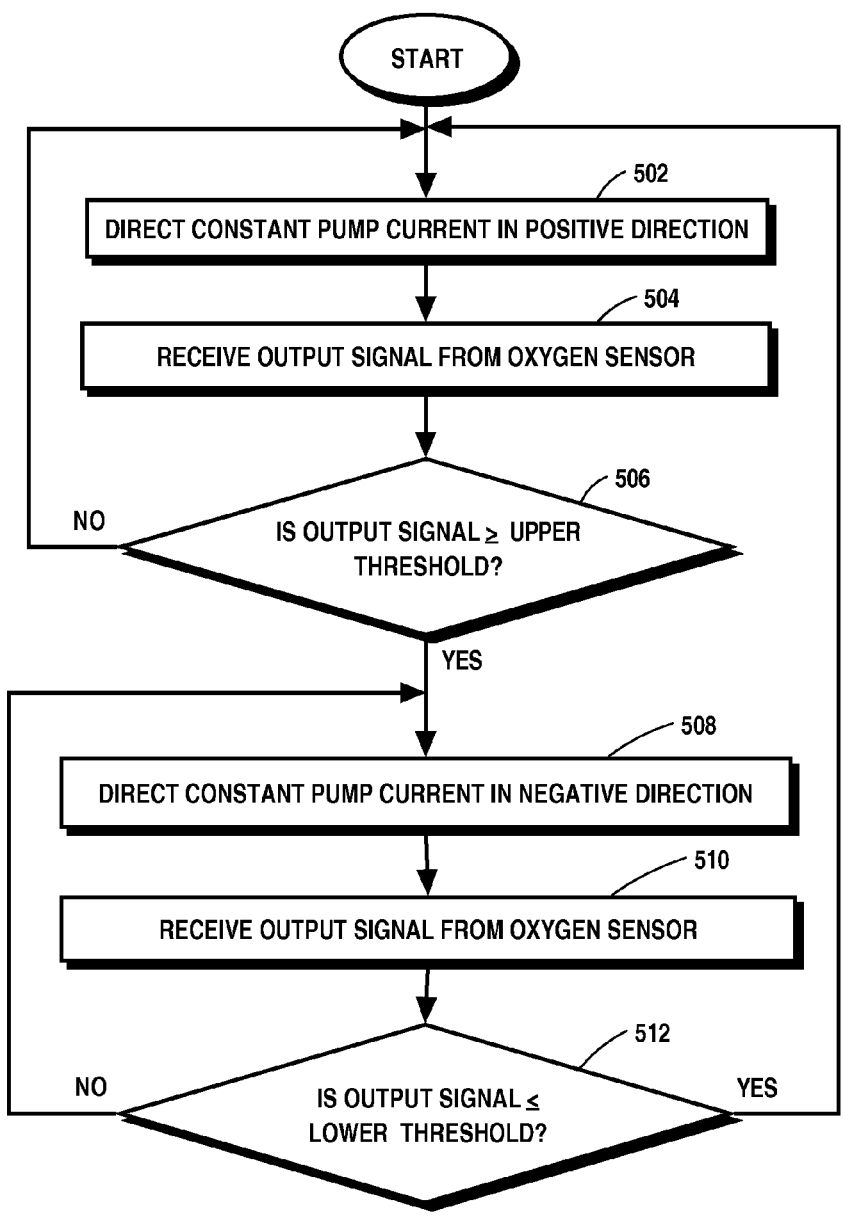
FIG. 5 is a flow chart of a method of varying the oxygen ion flow within the measuring cell in accordance with the exemplary embodiment.

FIG. 5 is a flow chart of a method of varying the oxygen ion flow within the measuring cell 202 in accordance with the exemplary embodiment. The flow chart of FIG. 5, therefore, illustrates an exemplary method of performing step 404 of FIG. 4. Although the discussion with reference to FIG. 5 is directed to oxygen sensors, the teachings can be applied to other types of wideband sensors.

At step 502, the pump current 208 is directed in a positive direction through the pump cell 204 at a constant magnitude. In the exemplary oxygen monitoring device 200 described with reference to FIG. 3, the analog switch 316 remains closed as positive voltage is applied across the pump cell 204. The positive voltage is maintained until the analog comparator circuit 304 triggers the inverting amplifier 308 to applying a negative voltage across the pump cell 204.

At step 504, the output signal from the oxygen sensor cell 224 is received. In the exemplary oxygen monitoring device 200, the output of the oxygen sensor cell 224 is received through the resistor ($R_1$) 324 at the positive input of the operational amplifier 322 of the analog comparator circuit 304.

At step 506, it is determined whether the output signal is greater than or equal to the upper threshold. If the upper threshold has not been reached, the method returns to step 502 where the constant positive pump current is directed through the pump cell 204. If the upper threshold has been reached, the method continues at step 508 where the current is reversed and a constant pump current 208 is directed in the negative direction. As discussed above with reference to FIG. 3, in the exemplary embodiment, the current managing device 216 includes an analog comparator circuit 304 and an inverting amplifier circuit 306 to provide the constant current until the thresholds are reached. The analog comparator circuit 304 triggers the reverse of the pump current 208 in response to the detection that the thresholds have been reached. Therefore, the positive pump current (IP+) is maintained until the output of the oxygen sensor cell 224 reaches an upper threshold that causes the output of the analog comparator circuit 304 to switch to a high output changing the output of the inverting amplifier circuit 306.

At step 508, the pump current 208 is directed in a negative direction. In response to the reversed voltage output of the inverting amplifier circuit 306 the pump current 208 reverses direction and becomes negative (−Ip).

At step 510, the current managing unit 216 receives the output signal from the oxygen sensor cell 224. In the exemplary oxygen monitoring device 222, the output of the oxygen sensor cell 224 is received through the resistor ($R_1$) 324 at the positive input of the operational amplifier 322 of the analog comparator circuit 304.

At step 512, it is determined if the output signal is less than or equal to the lower threshold. Of the lower threshold has not yet been reached, the method returns to step 508 where the current managing unit 218 continues to direct the pump current 208 in a negative direction through the pump cell 204. Otherwise, the procedure returns to step 502, where the current is reversed to the positive direction. Accordingly, in the exemplary embodiment, the current managing device 216 varies the current between 0.445 volts and 455 volts based on the output of the oxygen sensor cell 224. As the pump current 208 is varied, characteristics of the resulting square wave are measured and stored.

In the exemplary embodiment, the computing device 218 monitors the time periods ($t_1$ and $t_2$) and if either of the time periods exceeds a operating threshold, the computing device 218 overwrites the ENABLE signal and disconnects the pump cell 204 to prevent damage to the sensor. A diagnostic procedure is performed to determine the fault condition.

Figure 6:
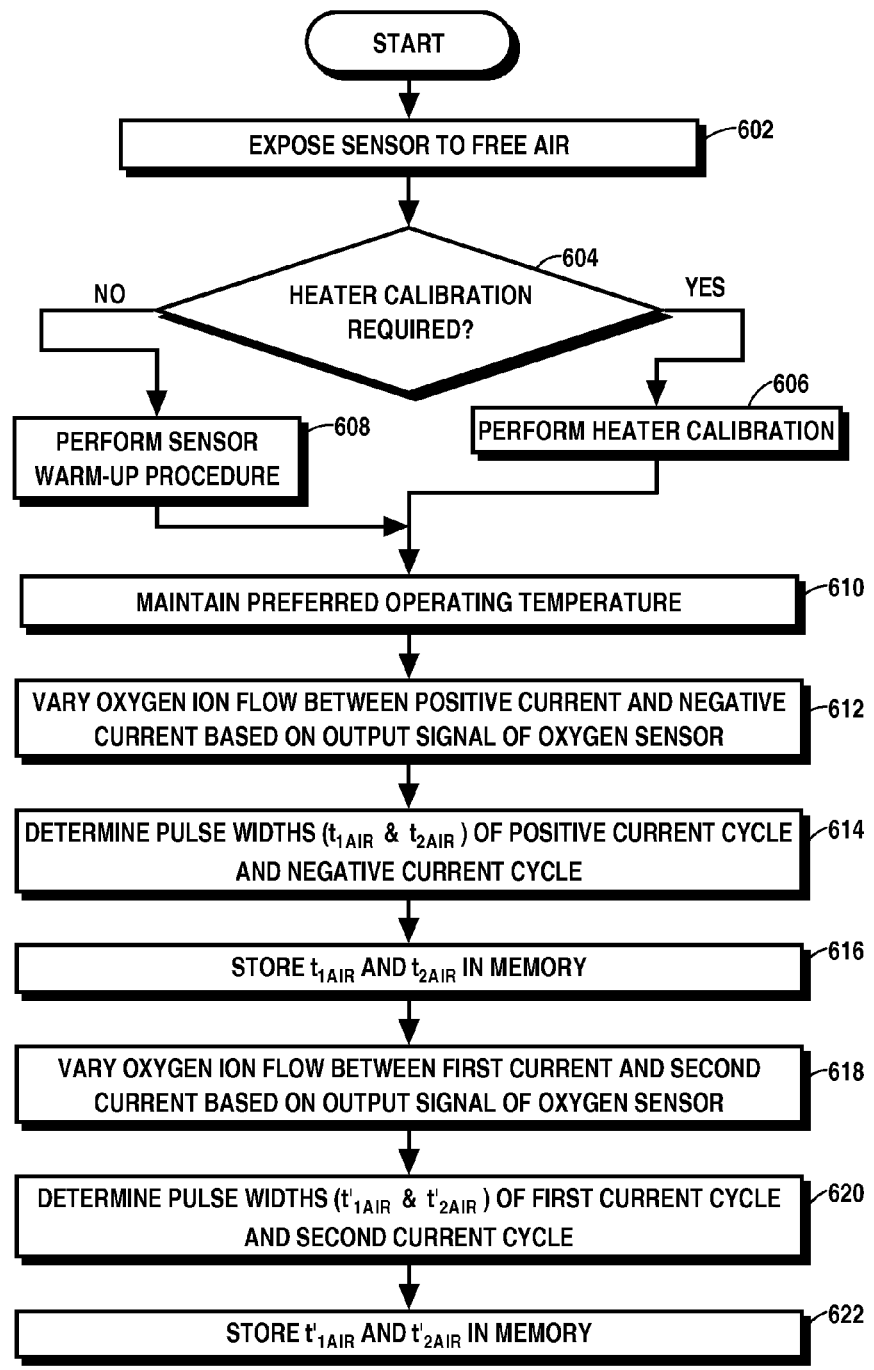
FIG. 6 is a flow chart of a method of calibrating an oxygen measuring device in accordance with the exemplary embodiment.

FIG. 6 is a flow chart of an exemplary method of calibrating the oxygen monitoring device 222. The method described with reference to FIG. 6 provides and exemplary method of performing the calibration step 402 of FIG. 4. The oxygen monitoring device 222 may be calibrated in any number of ways and the particular calibration method used may depend on a variety of factors such as the characteristics of the particular sensor 202 and the data that will be collected using the oxygen monitoring device 222. In the exemplary embodiment, the calibration procedure includes calibrating the heater control unit 302 and determining the pulse widths of the varying pump current 208 when the oxygen sensor cell 224 is exposed to free air. Although the discussion with reference to FIG. 6 is directed to oxygen sensors, the teachings can be applied to other types of wideband sensors.

At step 602, the oxygen sensor cell 224 is exposed to free air. In the exemplary embodiment, the measuring cell 202 is placed in an area where exposure to exhaust gases or other air borne impurities is minimized. In some circumstances where the oxygen measuring device 222 is operating in a functioning vehicle, the computing unit determines that the engine is in a coast down mode when the resulting lambda value is above the lean burn limit for gasoline and not changing over some period of time. When it is determined that the vehicle is in a coast down mode, the computing device 218 performs the calibration procedure. If the computing device 218 is the ECU itself, the coast down condition is already known and the ECU, after the predetermined purge time of the exhaust system, performs the calibration procedure for free air.

At step 604, it is determined whether the heater control unit 302 should be calibrated. In the exemplary embodiment, the heater control unit 302 is calibrated during the powering up sequence. Examples of other suitable situations that require the heater calibration procedure to be performed include the replacement or reconnection of the measuring cell 202 and the detection of certain measurement errors. If heater calibration is required, the procedure continues at step 606. Otherwise, the proceeds directly to step 608.

At step 606, the heater control unit 302 is calibrated. In the exemplary embodiment, a preferred heater impedance and a preferred pump cell impedance corresponding to a preferred operating temperature of the Nernst cell (224) are stored in memory. As discussed with reference to FIG. 8, the Nernst cell impedance is maintained at a target Nernst cell impedance for a suitable time period before the preferred heater impedance and the preferred pump cell impedance are measured and recorded.

At step 608, a sensor warm-up procedure is performed. In the exemplary monitoring device described with reference to FIG. 3, the analog switch 316 is initially opened during the sensor warm-up procedure. In accordance with the appropriate heating timetable, power is applied to the heater element 330 to increase the temperature. The heater control unit 302 monitors the current and voltage across the heating element 330 and determines the impedance of the heater element 330. The heater impedance is compared to the preferred heater impedance that was measured and stored during the heater calibration procedure. When the heater control unit detects that the heater impedance is equal to the preferred heater impedance, the heater control unit 302 determines that the minimum operating temperature of the oxygen sensor cell 206 has been reached. In response to a determination that the desired operating temperature is reached, the heater control unit 302 presents a "high" enable signal at the "Ready" output. The AND gate (U3) 318 closes the analog switch 316 when the ENABLE signal goes "high".

At step 610, the preferred operating temperature of the Nernst cell is maintained. The preferred operating temperature is maintained during the remainder of the oxygen sensor calibration procedure as well as during operation of the oxygen monitoring device 222. In the exemplary embodiment, the pump cell 204 impedance $R_{PUMP}$ is constantly monitored during operation and the heater control unit 302 is controlled to maintain a constant, or nearly constant, preferred pump cell impedance. The preferred pump cell impedance is retrieved from memory where it was stored during the heater calibration procedure. An example of a suitable method of controlling the heater control unit 302 includes using pulse width modulation to increase or decrease the amount of power dissipated by the heater element 330.

When the oxygen measuring device 222 is in an oscillating mode and the current is varied, the voltage at the pump cell 204 (output of $U_2$) is determined by Vcc, $R_{PUMP}$, the resistor $R_4$ 310, and the back-EMF of the pump cell 204. The output of the operational amplifier ($U_1$) 322 of the analog comparator circuit 304 switches between 0V and Vcc. The heater control unit 302 samples the output of the operational amplifier ($U_2$) 308 before and after each transition of the output of the operational amplifier ($U_1$) 322. The absolute value of the difference between the voltage measured before and after each transition is $U_{DIFF}$. In some circumstances, the output of the operational amplifier ($U_2$) 308 is passed through a high pass filter (not shown) of sufficiently high cut-off frequency. The filter output is sampled immediately after the transition point and the absolute value of resulting output voltage is equal to $U_{DIFF}$.

The heater control unit 302 calculates the pump cell 204 impedance $R_{PUMP}$ in accordance with the following relationship:

$$R_{PUMP} = R_4(U_{DIFF}/Vcc) \quad (1)$$

In some circumstances, the Nernst cell (224) impedance ($R_N$) is monitored as an alternative or in addition to monitoring the pump cell 204 impedance. In order to monitor the Nernst cell (224) impedance, the output voltage signal of the Nernst cell (224) is passed through a high pass filter and amplifier (not shown). The resulting filtered and amplified signal is then sampled at the comparator transition point. The peak-peak voltage, $U_{NPP}$, is then calculated as the difference between the sample voltage at low-high and high-low transition.

The voltage $U_{NPP}$ follows the equation:

$$U_{NPP} = Vcc(R_1 + 2R_N)/R_2 \quad (2)$$

$U_{NPP}$, therefore, linearly follows the Nernst cell (224) impedance, $R_N$, and is a convenient measurement for the Nernst cell (224) impedance without the use of any filtering in the signal path to influence the measured lambda signal. The resistors, $R_1$ and $R_2$, are chosen such that the current through $R_N$ is small enough to not influence the function of the Nernst cell (224) and such that the $U_{NPP}$ at the Nernst operating temperature and impedance is approximately 10 mV.

At step 612, the oxygen ion flow 210 is varied between a positive current (Ip) and the negative current (−Ip) based on the output signal of the oxygen sensor cell 224. An example of suitable method of varying the current 208 is described above with reference to FIG. 5.

At step 614, the pulse width ratio for air ($PWM_{AIR}$) is determined. In the exemplary embodiment, the pulse widths ($t_{1AIR}$ and $t_{2AIR}$) are determined for the positive current cycle and the negative current cycle. The transition times of the square wave are timed by a crystal clock within the computing device 218 to measure the pulse widths. The values for the pulse widths are measure and averaged over a sufficient time period such as one second, for example, to calculate an average $PWM_{AIR}$.

If the pulse width ratio for air is calculated during a coast down condition, the computing device 218 determines when the condition is reached before measuring the pulse widths of the pump current 208. If the computing device 218 is an ECU in the system, the ECU detects the condition based on parameters directly available to the ECU such as throttle position and engine speed.

At step 616, $PWM_{AIR}$ is stored in memory. Various techniques may be used to store and retrieve calibration information. For example, the pulse widths ($t_{1AIR}$ and $t_{2AIR}$) may be stored directly into memory and used for calculating $PWM_{AIR}$ at a later time. Such a procedure may be desired where the frequency of the square wave is used to further compensate for pressure and temperature variations. By storing the pulse width timing, frequency information is stored in addition to the average pulse width ratio for air ($PWM_{AIR}$).

At step 618, the oxygen ion flow 210 is varied between a first current and second current based on the output signal of the oxygen sensor cell 206. In the exemplary embodiment, the current 208 is varied between (IP) and zero. In a manner similar to the method described above, the current 208 is varied from a first current to a second current except that a zero current is used in place of the negative current (IP−).

At step 620, the pulse width ratio for air when the second current is zero ($PWM'_{AIR}$) is determined. In the exemplary embodiment, the pulse widths ($t'_{1AIR}$ and $t'_{2AIR}$) are determined for the positive current cycle and the zero current cycle. The transition times of the square wave are timed by a crystal clock within the computing device 218 to measure the pulse widths. The values for the pulse widths are measure and averaged over a sufficient time period such as one second for example to calculate an average $PWM'_{AIR}$. To measure $PWM_{AIR}'$, the computing device 218 sets the signal CALIBRATE high. The NAND-Gate ($U_4$) 328 together with AND-Gate ($U_3$) 318 thus cause the analog switch 316 to switch on only during the high phase of the pump current 208. During the low phase, the analog switch 316 is off and no pump current can flow.

At step 622, $PWM'_{AIR}$ is stored in memory. Various techniques may be used to store and retrieve calibration information. For example, the pulse widths ($t'_{1AIR}$ and $t'_{2AIR}$) may be stored directly into memory and used for calculating $PWM'_{AIR}$ at a later time.

Other calibration procedures may be performed in some situations. Calibration procedures for pressure and temperature compensation, for example, may be performed by measuring and storing frequency information corresponding to the pump current 208 at certain calibration conditions.

Figure 7:
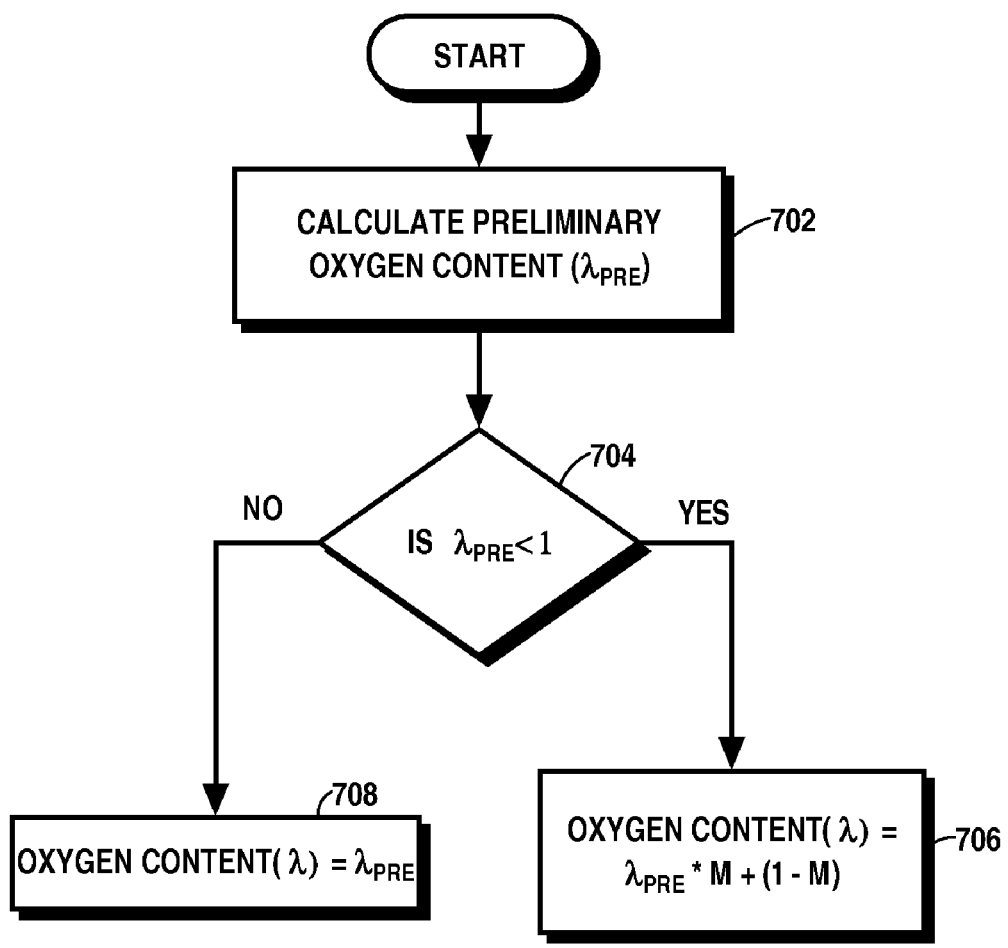
FIG. 7 is a flow chart of a method of determining the oxygen concentration of a gas by comparing the measured pulse width ratio ($PWM_{RATIO}$), to the pulse width ratio function in accordance with the exemplary embodiment of the invention.

FIG. 7 is a flow chart of a method of determining the oxygen concentration of a gas by comparing the measured pulse width ratio, $PWM_{RATIO}$, to the pulse width ratio function in accordance with the exemplary embodiment of the invention. The method described with reference to FIG. 7 is an exemplary method of performing step 408 of FIG. 4. Although the discussion with reference to FIG. 7 is directed to oxygen sensors, the teachings can be applied to other types of wideband sensors.

At step 702, a preliminary oxygen concentration, ($\lambda_{PRE}$) is calculated. In the exemplary embodiment, the preliminary oxygen concentration ($\lambda_{PRE}$) is determined by the following equation:

$$\lambda_{PRE} = P/(PWM_{AIR} - PWM_{RATIO}) \quad (3)$$

$$\text{where } P = (1 + PWM'_{AIR})(1 - PWM_{AIR})/(1 - PWM'_{AIR}) \quad (4)$$

The computing device 218 retrieves from memory the values for $PWM_{AIR}$, $PWM_{RATIO}$, and $PWM'_{AIR}$ and applies the above equations to calculate the preliminary oxygen concentration, $\lambda_{PRE}$. As explained below, P is equal to $PWM_{AIR}$ where the pulse width ratio at the stoichiometric ratio ($PWM_{ST}$) is zero. Therefore, $\lambda_{PRE}$ is equal to $PWM_{AIR}/(PWM_{AIR} - PWM_{RATIO})$ where the $PWM_{ST}$ for the particular sensor is zero.

At step 704, it is determined whether $\lambda_{PRE}$ is less than one. If $\lambda_{PRE}$ is less than one, the procedure continues at step 706. Otherwise, the procedure continues at step 708, where the oxygen concentration (λ) of the gas is determined to be equal to the preliminary oxygen concentration, $\lambda_{PRE}$.

At step 706, the oxygen concentration (λ) of the gas is determined to be equal to the sum of the preliminary oxygen concentration ($\lambda_{PRE}$) multiplied by a calibration factor (M) and 1 minus the calibration factor ($\lambda=(\lambda_{PRE})*M+(1-M)$). In the exemplary embodiment, a calibration factor, M, for the brand and model of the particular measuring cell 202 is derived through statistical analysis of the measuring cell's 202 performance when exposed to a gas with a known oxygen concentration. In some circumstances, a calibration factor for each of several measuring cells is stored in memory and applied to the particular model that is connected within the oxygen measuring device 222. An example of typical value of M is 0.71428.

Figure 8:
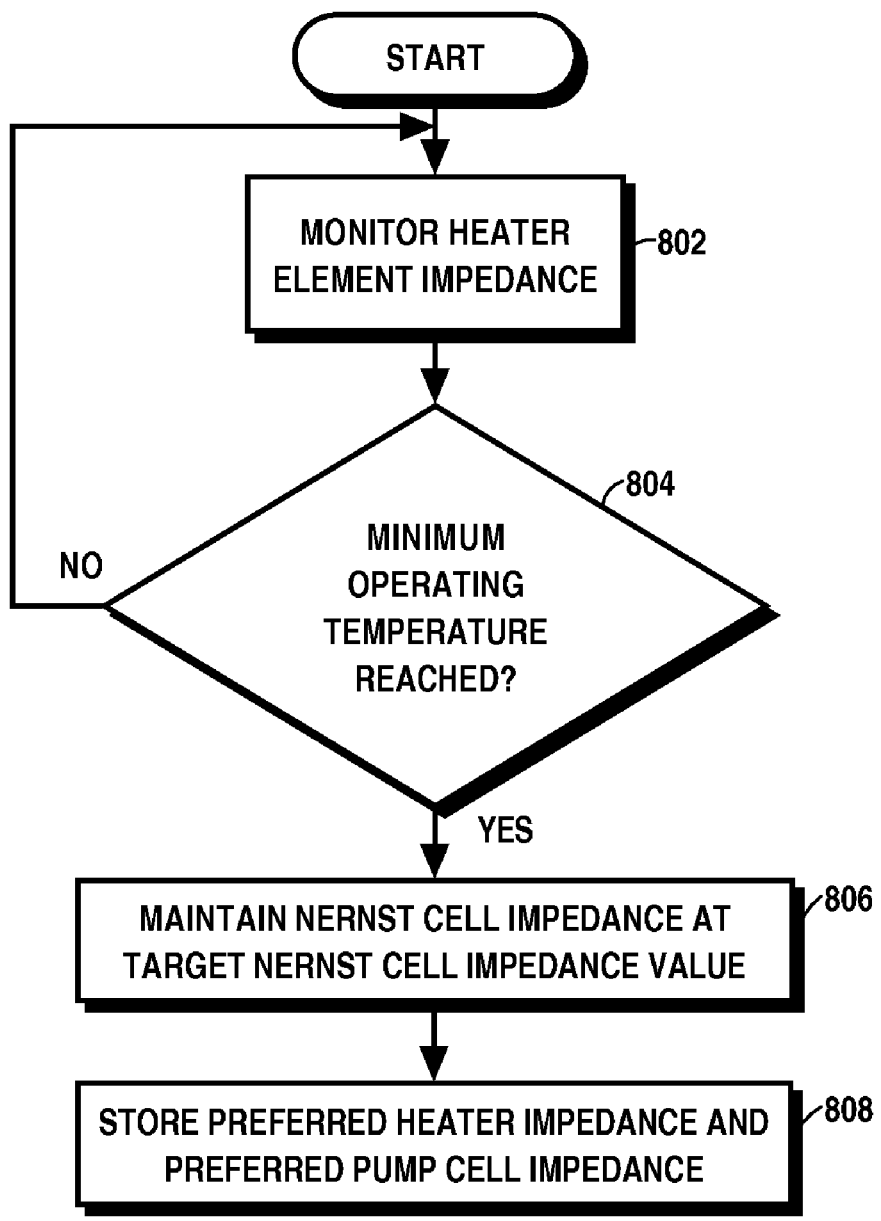
FIG. 8 is a flow chart of a method of calibrating the heater control unit in accordance with the exemplary embodiment of the invention.

FIG. 8 is flow chart of an exemplary method of calibrating the heater control unit 302. The method discussed with reference to FIG. 8, therefore, provides an exemplary method for performing step 606 of FIG. 6. Although the discussion with reference to FIG. 8 is directed to oxygen sensors, the teachings can be applied to other types of wideband sensors.

At step 802, the heater element 330 impedance is monitored as the temperature of the heater element 330 is increased. In the exemplary monitoring device described with reference to FIG. 3, the analog switch 316 is initially opened during the heater unit calibration procedure. In accordance with the appropriate heating timetable, power is applied to the heater element 330 to increase the temperature. The heater control unit 302 monitors the current and voltage across the heating element and determines the impedance of the heater element. Based on stored information relating the heater element impedance to the temperature of the heater element 330, the heater control unit determines when the minimum operating temperature of the oxygen sensor cell 224 is reached. In response to a determination that the desired minimum operating temperature is reached, the heater control unit 302 presents a "high" enable signal at the "Ready" output. The AND gate (U3) 318 closes the analog switch 316 when the ENABLE signal goes "high".

At step 804 it is determined whether the minimum operating temperature has been reached. The procedure proceeds to step 806 when the minimum operating temperature is reached. Otherwise, the heater temperature continues to be monitored at step 802 with the analog switch 316 opened.

At step 806, the Nernst cell impedance is maintained at the target Nernst cell impedance. The heater control unit 302 is controlled such that the temperature is varied to maintain the Nernst cell impedance at the target value. The target Nernst cell impedance is a predetermined value that depends on the type and brand of the measuring cell (sensor) 202 and is provided by the sensor manufacturer. The Nernst cell impedance is held constant or nearly constant for a minimum time to allow fluctuations in temperatures and impedances to settle. An example of a suitable settling time is ten seconds.

As described above, the Nernst cell (224) impedance is monitored by passing the output voltage signal of the Nernst cell (224) through a high pass filter and amplifier (not shown). The resulting filtered and amplified signal is sampled at the comparator transition point. The peak-peak voltage, $U_{NPP}$, is calculated as the difference between the sample voltage at low-high and high-low transition in accordance with Equation 2.

At step 808, the preferred heater impedance and the preferred pump cell impedance are measured and stored. In the exemplary embodiment, the pump cell impedance is calculated based on Equation 1. As discussed above, the voltage at the pump cell 204 (output of $U_2$) is determined by Vcc, $R_{PUMP}$, the resistor $R_4$, and the back-EMF of the pump cell 204 when the oxygen measuring device 222 is in an oscillating mode. The output of the operational amplifier ($U_1$) 322 of the comparator 304 switches between 0V and Vcc. The heater control unit 302 samples the output of the operational amplifier ($U_2$) 308 before and after each transition of the output of the operational amplifier ($U_1$) 322. The absolute value of the difference between the voltage measured before and after each transition is $U_{DIFF}$. In some circumstances, the output of the operational amplifier ($U_2$) 322 is passed through a high pass filter (not shown) of sufficiently high cut-off frequency. The filter output is sampled immediately after the transition point and the absolute value of resulting output voltage is equal to $U_{DIFF}$.

Although various calibration factors and equations may be used depending on the particular implementation of the oxygen measuring device, the above equations are derived based on the following analysis and assumptions in the exemplary embodiment. Those skilled in the art will recognize the modifications based on the teachings herein.

The relationships between the various parameters are described below with reference to equations 5-26 where the following is assumed:

$Q_f$ is the required oxygen flow in and out of the measuring cell 202 to maintain the Nernst cell (206) at the transition point;

$Q_1$ is an oxygen flow value out of the Nernst cell (224) at the fixed constant current (Ip);

$Q_2$ is an oxygen flow value into the Nernst cell (224) at the fixed constant current (−Ip);

$t_1$ is the oxygen pump time ($Q_1$ flow) required to switch the Nernst cell (224) from 0.445V to 0.455V; and $t_2$ is the oxygen pump time ($Q_2$ flow) required to switch the Nernst cell (224) from 0.455V to 0.445V.

For the forgoing assumptions, therefore, the Nernst cell (206) voltage is 0.45V with an alternating current (AC) component of 10 mVpp. The resulting $Q_f$ is:

$$Q_f=(Q_1*t_1-Q_2*t_2)/(t_1+t_2) \quad (5)$$

The timing relationships can be expressed as $$PWM_{RATIO}=(t_1-t_2)/(t_1+t_2) \quad (6)$$

Using 1 and 2, equation 1 can be rewritten as:

$$Q_f=[(Q_1+Q_2)*PWM_{RATIO}+Q_1-Q_2)]/2 \quad (7)$$

Pump flow ratio ($Q_{RAT}$) can be expressed as:

$$Q_{RAT}=(Q_1-Q_2)/(Q_1+Q_2) \quad (8)$$

At changing air pressure, $Q_1$ and $Q_2$ change approximately proportionally and, therefore, $Q_{RAT}$ stays nearly constant. The same holds true for temperature changes. Accordingly, $Q_{RAT}$ is independent of temperature.

In some circumstances, $Q_{RAT}$ may change when the sensor ages and, therefore, the sensor may need to be periodically calibrated to maintain optimal performance.

If $Q_1$ and $Q_2$ are known and are constants, the oxygen flow rate and Lambda, (λ) is determined from the timing relationship, $PWM_{RATIO}$, which is measured. $Q_1$ and $Q_2$ are constant if the pump current 208, temperature, exhaust pressure, barometric pressure and oxygen concentration in air are constant. In the exemplary embodiment, the pump current 208 and temperature are held constant through careful circuit design. For the analysis described herein, the atmospheric oxygen concentration is assumed to be constant at 20.9%. Barometric pressure effects are compensated through calibration. The effect of exhaust pressure tends to modify both, $Q_1$ and Q2 by an equal factor and also modifies the response time of the oxygen sensor cell 206 because more or less oxygen ions are present at the oxygen sensor cell 206 surface depending on pressure.

As described above, the oxygen monitoring device 222 measures oxygen flow by switching the pump current 208 between a constant positive and negative value. The absolute value for this constant pump current value is chosen such that it is greater than the absolute value of the pump current 208 required for free air.

The above equation is linear and can be determined with two known points. The time values $t_1$ and $t_2$ are measured by a crystal controlled microprocessor or timer circuit which allows the accurate determination of Lambda, ($\lambda$), once the two calibration points are known.

A stoichiometric exhaust mixture does not require any corrective oxygen flow and the steady state pump current 208 is, therefore, equal to zero. This condition is used to determine one of the calibration points, the stoichiometric pulse width ratio, $PWM_{ST}$.

As described above, a second calibration point is obtained by measuring the pulse width ratio when the measured gas is air. The measuring cell 202 is exposed to free air. If the measuring cell 202 is not installed in a vehicle, the measuring cell is placed in an area exposed to free air. If the measuring cell 202 is installed in a vehicle, the calibration for free air is performed when the vehicle has not been in operation for an adequate time and all the exhaust gases have dissipated or when the vehicle is in a cost-down mode. During the coast-down mode, the throttle on the engine is completely closed and engine speed is above a predetermined value. In this case, a typical ECU will not inject any fuel because no power output is required from the engine and further fuel can be saved. The pump cell 204 is then driven with a total flow value $Q_F$ that is high enough to pump all oxygen from the air in the measurement chamber.

From equations 5 through 8 follows:

$$PWM_{ST} = -Q_{RAT} \quad (9)$$

The lambda value, $\lambda$, calculated from exhaust oxygen concentration can be expressed as:

$$\lambda = \text{Air Oxygen content}/(\text{Air Oxygen content} - \text{Excess Oxygen}) \quad (10)$$

Note that the value Excess Oxygen in Equation 6 can have negative values if all oxygen is consumed but unburned or partially burned fuel is still present.

To examine the oxygen flow rate instead of volume, t is eliminated by division:

$$\lambda = Q_{f(AIR)}/(Q_{f(AIR)} - Q_f): \quad (11)$$

applying equations 7, 8, 9, and 11:

$$\lambda = (PWM_{AIR} - PWM_{ST})/(PWM_{AIR} - PWM_{RATIO}) \quad (12)$$

As described above, a second free air PWM ratio ($PWM'_{AIR}$) is measured by switching the pump cell 204 between $Q_1$ and no current ($Q_2=0$) during free air calibration.

$PWM_{ST}$ is calculated during calibration from $PWM_{AIR}$ and $PWM'_{AIR}$ according to the following formulas:
From equation 7, $$2*Q_f = (Q_1 + Q_2)*PWM_{AIR} + Q_1 - Q_2 \quad (13)$$

$$2*Q_f = Q_1*PWM'_{AIR} + Q_1 \quad (14)$$

Where $PWM'_{AIR}$ is measured when switching between $Q_1$ and no current instead of $Q_1$ and $Q_2$.

$$P = PWM_{AIR} - PWM_{ST} \quad (15)$$

From equations 13 and 14:

$$P = (1 + PWM'_{AIR})*(1 - PWM_{AIR})/(1 - PWM'_{AIR}) \quad (16)$$

$$PWM_{ST} = PWM_{AIR} - P \quad (17)$$

Applying equation (12):

$$\lambda = P/(PWM_{AIR} - PWM_{RATIO}) \quad (18)$$

As explained above, $PWM_{AIR}$ is measured by exposing the sensor to free air at the appropriate operating temperature and, in some circumstances, frequency information is used for determining compensation factors. The following analysis demonstrates the relationship between frequency and other parameters.

Returning to equation 8, if $Q_1 = Q_2$, $Q_{RAT}$ (and therefore $PWM_{ST}$) becomes zero. The actual sampling frequency is dependent on the full flow ratio, $Q_F$.

Equation 8 then changes to:

$$Q_f = Q_F * PWM_{RATIO}. \quad (19)$$

Equation 12 becomes $$\lambda = PWM_{AIR}/(PWM_{AIR} - PWM_{RATIO}) \quad (20)$$

$Q_F$ is a function of the pump current 208, Ip, and, therefore, $Q_F = f(Ip)$. If $Q_F$ for a constant Ip changes because of exhaust pressure changes, the measured $PWM_{RATIO}$ becomes $PWM'_{RATIO}$ for the same corrective flow, $Q_f$.

With exhaust gas pressure or temperature changes $Q_1$ and $Q_2$ change by a factor K in a first approximation.

Equation 8 then becomes:

$$Q_f = K*[(Q_1 + Q_2)*PWM'_{AIR} + Q_1 - Q_2)]/2 \quad (21)$$

where $$Q_1 * t_1 = K*Q_1*t_1' \quad (22)$$

$$Q_2 * t_2 = K*Q_2*t_2' \quad (23)$$

The measurement frequency f is determined by:

$$f = 1/(t_1 + t_2) \quad (24)$$

$$f' = 1/(t_1' + t_2') \quad (25)$$

From equations 20, 21, 22 and 23 follows:

$$K = f'/f \quad (26)$$

Because f is constant when all other environmental conditions are constant, this calculation can be used to correct for temperature and/or pressure changes. Equation 8 then becomes:

$$\lambda = (PWM_{AIR} - PWM_{ST})/(PWM_{AIR} - (1-K)*PWM_{ST} - K*PWM'_{RATIO}) \quad (27)$$

and equation 18 becomes:

$$\lambda = PWM_{AIR}/(PWM_{AIR} - K*PWM'_{RATIO}) \quad (28)$$

These equations, therefore, allow the application of a pressure compensation factor, K to compensate for pressure or temperature changes. Under extreme circumstances, $Q_1$ and $Q_2$ do not change equally by the same factor K. In some situations, therefore, the normalized frequency deviation f'/f is used as an index into an experimentally derived lookup table to extract the accurate deviation factor K':

$$K' = func(f'/f) \quad (29)$$

The calculated Lambda value can thus be corrected for exhaust pressure changes without the use of separate sensors to measure exhaust pressure once a normalized frequency/lambda table is experimentally determined for a given sensor type.

Conventional commercially available packaged measuring cells 202 often have temperature dependent parasitic resistances to the virtual ground of the pump cell 204 and Nernst cell (224). This parasitic resistance must be addressed through software or circuitry in order to apply pressure compensation methods described above with many commercially available measuring cells 202.

The forgoing equations and analysis may be applied to other implementations of the invention in ways other than described above and the teachings described herein may be applied to a variety of formats, implementations and configurations. As explained above, the hardware and software may be modified to accommodate a variety of factors. For example, the analog switch 316 can be eliminated where the operational amplifier ($U_2$) 308 provides a tri-state output. Also, the analog switch 316 can be connected within the oxygen measuring device 222 before the inverting resistor ($R_4$) 310 instead of connecting to the output of the operational amplifier ($U_2$) 308. The operational amplifier ($U_2$) 308 may also provide a tri-state output. In addition, the heater controlling unit 302 may be integrated as part of the computing device 218.

Further, the Zener diode 314 may be replaced with a digital to analog (D/A) converter or a potentiometer in some circumstances. The references voltage $U_{REF}$ could thereby be set such that the pulse width ratio at the stoichiometric ratio, $PWM_{ST}$ is exactly zero. In such a circumstance, the equation used to calculate $\lambda$ is:

$$\lambda = PWM_{AIR}/(PWM_{AIR} - K*PWM') \qquad (30)$$

In some circumstances, frequency information is analyzed to provide other useful information or data in accordance with the analysis above. For example, because the response time of a measuring cell 202 changes with aging, the oscillating frequency is used directly as a measurement to determine the need for replacement. When a lower threshold frequency is reached, the computing device 218 may provide a warning that the sensor should be replaced. The frequency analysis is preferably performed when the free-air value is recalibrated because the environmental conditions are comparable (f' and f in equation 27 are equal) and the frequency change is due to aging of the sensor.

Figure 9:
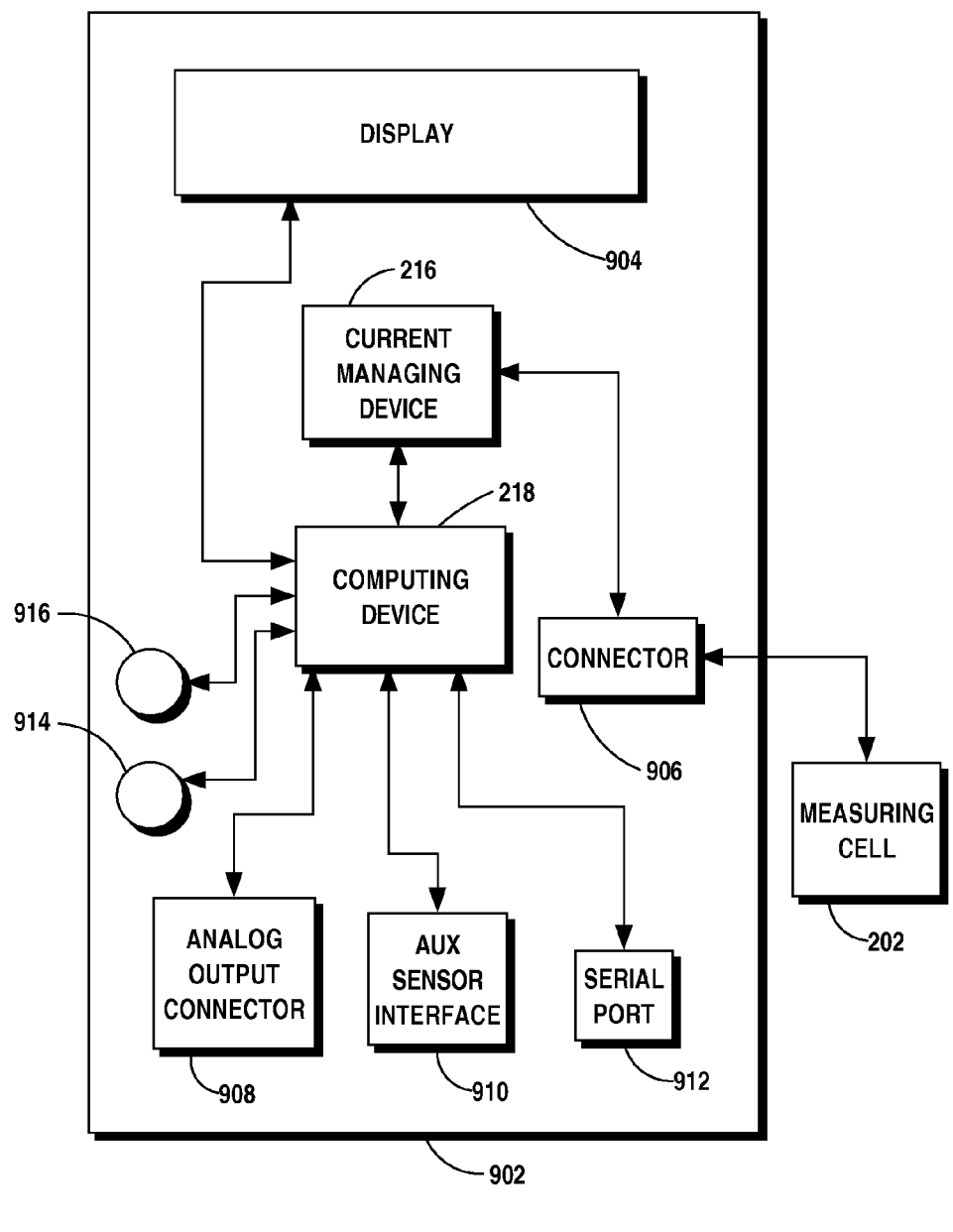
FIG. 9 is a block diagram of a hand-held diagnostic device suitable for embodying the oxygen measuring device.

FIG. 9 is a block diagram of an exemplary hand-held diagnostic device suitable for embodying the oxygen measuring device 222. As mentioned above, the oxygen measuring device 222 may be implemented as any of several configuration and devices. The oxygen measuring device 222, for example, may be integrated as an OEM device in a vehicle fuel system. Further, the oxygen measuring device 222 may be part of an in-vehicle aftermarket fueling system or diagnostic system. Other devices and uses will be readily apparent to those skilled in the art based on the teachings herein.

The exemplary hand-held diagnostic device 900 includes a housing 902, a display 904, connectors 906-912, and buttons (or other type of switches) 912, 914 that provide interfaces to the computing device 218 and the current managing device 216. The display allows the user to view information regarding the status to the hand-held diagnostic device 900. In the exemplary hand held device 900, the connectors 906-912 include a serial port 912 for connecting to an external computer, analog output connector 908 for supplying an analog signal corresponding to the measured $\lambda$, an auxiliary sensor interface 919, and a sensor connector 906. Other connectors such as a power connector for receiving DC supply power, for example, are also included in some circumstances. A calibrate button 908 connected to the computing device 218 provides a user interface for initiating the calibration procedure. A record button 914 provides a user interface for initiating a record procedure that allows several seconds of data to be stored in memory. An example of another button or switch that may be used includes an on-off switch (not shown). The buttons and connectors are connected to the computing device 218 and other circuitry and provide interfaces between the user, the measuring device 222, the measuring cell 202 and other external equipment.

Therefore, the system, apparatus and method for measuring the oxygen concentration of gas provides a cost effective, efficient and accurate way to monitor a gas having several advantages over conventional systems. The techniques described herein provide a simplified design since no analog to digital (A/D) conversion is required for a oxygen concentration ($\lambda$) measurement. Further, no calibration resistor is required in the measuring cell sensor to compensate for sensor tolerances which results in simplified production and lower production costs. Wide tolerances of the measuring cell 202 itself are acceptable, resulting in higher possible production yield. Because no precision resistors or other precision parts are required, circuit cost is minimized. The oxygen monitoring device 222 self-compensates for pressure and temperature variations. The measurement process is converted to the time-domain, instead of an analog current/voltage domain. By using standard crystal time bases, as is typical in digital designs, temperature and age-related drifts are eliminated because crystal time bases have tolerances of $<10^{-6}$ compared to $<10^{-2}$ for typical resistors. Measurement results are linear to 1/Lambda and independent of the Ip/Lambda curve of the sensor. Calibration is convenient and uses only air as a reference gas.

Although the discussion with reference to FIG. 9 is directed to a hand-held diagnostic device suitable for embodying the oxygen measuring device 222, the teachings can be applied to implement a handheld device for use with other types of wideband sensors. For example, the device 900 may be configured to connect to measuring cell that is responsive to nitrogen or to gaseous oxides of nitrogen.

Figure 10:
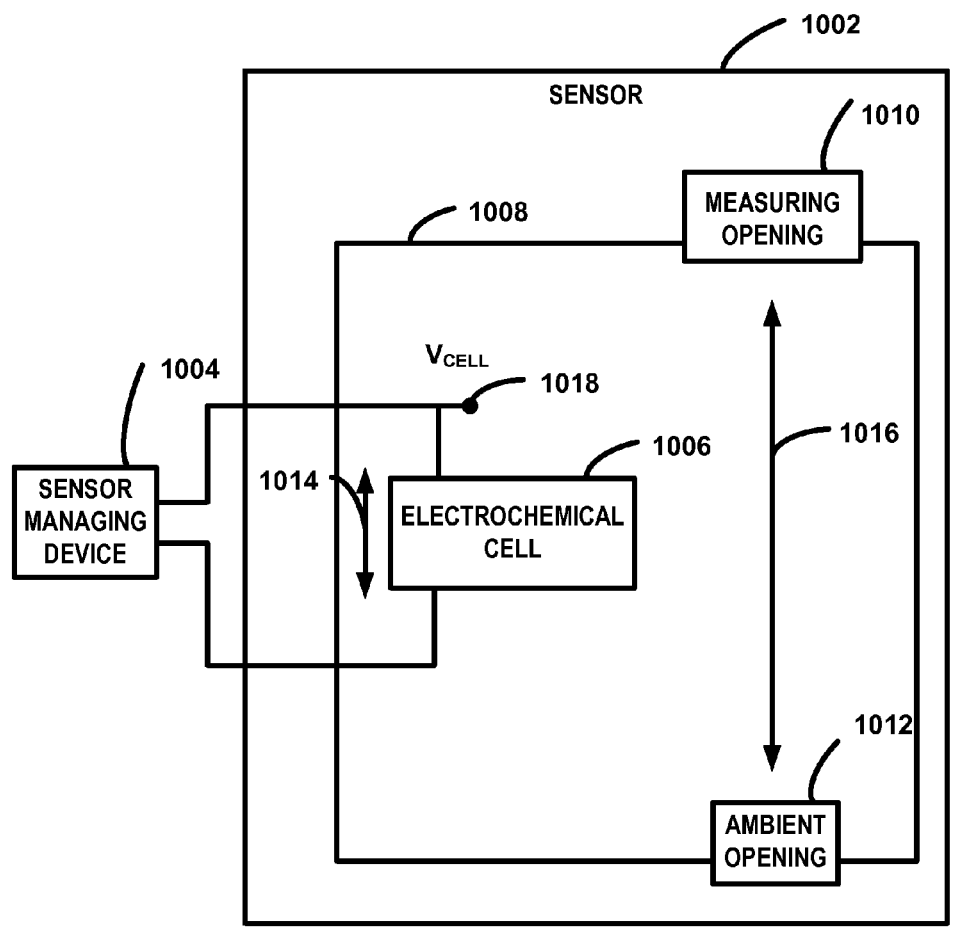
FIG. 10 is a block diagram of a sensor system including a sensor managing device connected to a wideband sensor in accordance with a second exemplary embodiment of the invention where a single electrochemical cell performs the functions of the sensor cell and measuring cell.

FIG. 10 is a block diagram of a sensor system 1000 including a sensor managing device 1004 connected to a wideband sensor 1002 in accordance with a second exemplary embodiment of the invention where a single electrochemical cell 1006 performs the functions of the sensor cell and measuring cell. The ion concentration measuring system includes a sensor that has a single electrochemical cell and a sensor measuring device that varies a pump current through the electrochemical cell between a first constant current and a second constant current in accordance with a cell voltage at the electrochemical cell. A measured fluid is received through a measuring opening to a measuring chamber of the sensor. The electrochemical cell moves ions between the measuring chamber and an ambient opening exposed to an ambient fluid, such as air, based on a pump current flowing through the electrochemical cell. A sensor measuring device determines the ion concentration of the measured fluid based on a cell voltage at the electrochemical cell. The internal resistance of the cell is determined and subtracted from the cell voltage to obtain the Nernst voltage of the electrochemical cell which indicates the ion concentration of the measured fluid.

The sensor system 1000 may be implemented using any combination of hardware, software and firmware. Various functions and operations of the functional blocks described herein may be implemented in any number of devices, circuits or elements. Any of the functional blocks may be integrated in a single device and the functions of the blocks may be distributed over several devices, circuits and elements.

The sensor 1002 includes an electrochemical cell 1006 connected within a measuring chamber 1008 having a measuring opening 1010 and an ambient opening 1012. A magnitude and direction of a pump current 1014 through the electrochemical cell 1006 is correlated to a flow of ions 1016 within the electrochemical cell 1006. The measuring opening 1010 of the measuring chamber 1008 is positioned to receive a measured fluid while an ambient opening 1012 faces an ambient fluid. The measured fluid and ambient fluid may be a gases or liquids. For the example presented herein, the measured fluid is a measured gas and the ambient fluid is ambient air where the measured gas is oxygen. The electrochemical cell 1006 is any device, component, or element that changes the ion concentrations within the measuring chamber 1008 based on the pump current 1014 flowing through the electrochemical cell and presents a voltage ($V_{CELL}$) that is correlated to the ion concentration. The electrochemical cell 1006 is similar to a pump cell in conventional sensors. In the exemplary embodiment, the electrochemical cell 1006 is a Nernst cell responsive to oxygen ions. The electrochemical cell 1006, however, may be responsive to other gases in some circumstances such as gaseous oxides of nitrogen, for example.

When a constant electrical current is forced through the electrochemical cell, a voltage is created at the cell which is the sum of the Nernst voltage and the voltage drop (resistance voltage) created by internal resistance of the electrochemical cell. The internal resistance is the real impedance of the cell sometimes referred to as the Ohmish impedance. The resistance voltage ($V_R$) results from the pump current flowing through the internal resistance. A Nernst voltage indicates the oxygen concentration in the measurement chamber and is equal to the difference between the total electrochemical cell voltage ($V_{CELL}$) and the resistance voltage ($V_R$). The Nernst voltage, therefore, can be calculated by subtracting the resistance voltage ($V_R$) from the electrochemical voltage ($V_{CELL}$). In the exemplary embodiment, the sensor managing device 1004 continually switches the pump current 1014 between positive and negative constant currents, measures the cell voltage, and determines the oxygen concentration based on the Nernst voltage by subtracting the resistance voltage ($V_R$). The sensor managing device 1004 includes a current managing unit 216 and a computing device 218 where the current managing unit controls 216 the current flow and measures the cell voltage. Accordingly, operation in the second exemplary embodiment is similar to the embodiment described above except that the pump cell and the measuring cell are replaced with a single electrochemical cell. The pump cell in the second exemplary embodiment, therefore, also acts as the measurement cell.

The electrochemical cell 1006 provides an output signal based on the number of ions within the measuring chamber 1008. In response to the output signal, the sensor managing device 1004 varies the pump current between two constant current levels. A first pump current is maintained by the current managing unit until the output signal reaches a first threshold. When the first threshold is reached, the current managing unit 1004 directs the pump current 1014 in the opposite direction until the output signal reaches a second threshold level. A computing device monitors the current fluctuation to determine an ion concentration of the measured fluid (gas). The pulse width ratio of the resulting oscillation is used as an indicator of oxygen flow through the pump cell. As discussed above, a suitable application of the sensor system 1000 includes a gas ion monitoring device for monitoring exhaust gas from a combustion engine to determine oxygen concentrations for adjusting an air-fuel mixture. The ion monitoring device, method, and system may be implemented as part of any of several types of applications and systems and may be used to measure any of numerous types of ions within a fluid medium. Some examples include measuring ion concentrations of gaseous oxides of nitrogen such as NO and NO2 ion levels, measuring carbon dioxide levels, measuring gas ion concentrations in liquids such as oxygen and carbon dioxide concentrations in water. Further, ion concentrations of salts and elements such as lead within liquids or gases may be measured in some situations. Accordingly, any of numerous types of ion concentrations may be measured where the ion sensor and current pump are responsive to the particular ions that are measured.

Accordingly, the measured voltage is used to trigger the reversal of pump current. For example, if during a positive pump current ($I_P$) the Nernst voltage ($|V_{CELL}|-|R*I_P|)>=0.5$ Volt, then the pump current ($I_P$) is reversed, R (internal resistance) is calculated as described below, and the process continues with a negative constant pump current until the Nernst Voltage is $<=0.4V$. Then the pump current ($I_P$) is polarized back to positive and so on. In this example, the Hysteresis voltage is 0.1V (0.5V −0.4V). Different Hysteresis Voltages can be used.

In the exemplary embodiment, the internal resistance (R) of the electrochemical cell is determined by measuring the voltage change at the cell at the transition point between positive and negative current and/or between negative and positive current through the cell. Since the pump current is switched between constant positive and negative currents, the resistance is calculated based on Ohms law.

The internal resistance is dependent on the temperature of the electrochemical cell. At a polarity reversal of the pump current, the cell has not had time to react and has not pumped any oxygen in the new direction. So the oxygen concentration difference, which determines the Nernst voltage, has not yet changed by a significant amount. Accordingly, the voltage change at the cell is at least mostly caused by the change in current. Based on the difference in current and difference in voltage, the internal resistance is determined based on the relationship $R_{CELL}=\Delta V_{CELL}/\Delta I_P$, where $\Delta V_{CELL}$ is the difference in voltage at the cell and $\Delta I_P$ is the difference in pump current. The internal resistance $R_{CELL}$ is used to determine the voltage drop ($V_R$) due to the internal resistance $R_{CELL}$ based on the Ohms Law, $V_R=R_{CELL}*I_P$. The resistance voltage ($V_R$) is subtracted from the actual voltage ($V_{CELL}$) on the electrochemical cell for the remainder of the cycle in subsequent calculations to determine the Nernst voltage and consequently the ion concentration. In most applications, the voltage change $\Delta V_{CELL}$ can be measured up to a few microseconds before and after the current transition. The difference between the voltage immediately before the polarity reversal and immediately after is the $\Delta V_{CELL}$ voltage change. A suitable technique for measuring the $\Delta V_{CELL}$ voltage includes using a sample and hold circuit.

The above discussion can be applied to an example as follows. If the absolute value of the pump current is 5 mA, and measured $\Delta V_{CELL}$ is 0.8 Volts ($I_P$ jumps from +5 mA to −5 mA. As delta Ip is 10 mA (+5 mA−(−5 mA)), $R_{CELL}$ is 80 Ohms. If the measurement chamber is slightly richer than stoichiometric (Nernst voltage is 0.5V), then the actual measured cell voltage at a jump from +5 mA to −5 mA jumps from 0.9V to 0.1V. Now the pump current is negative (−5 mA) and the pump cell pumps oxygen ions into the measurement chamber(s). This makes that chamber gradually leaner and the pump cell voltage decays. At the lower threshold of 0V (with a 0.1V hysteresis) the polarity of the current is reversed again and the voltage on the cell jumps to 0.8V (0.4V Nernst+

$V_R$ of 0.4V). Now oxygen ions are pumped again out of the chamber and the voltage across the pump cell rises again until it reaches the upper threshold of 0.9V (0.5V Nernst+$V_R$ of 0.4V) and so on.

Figure 11:
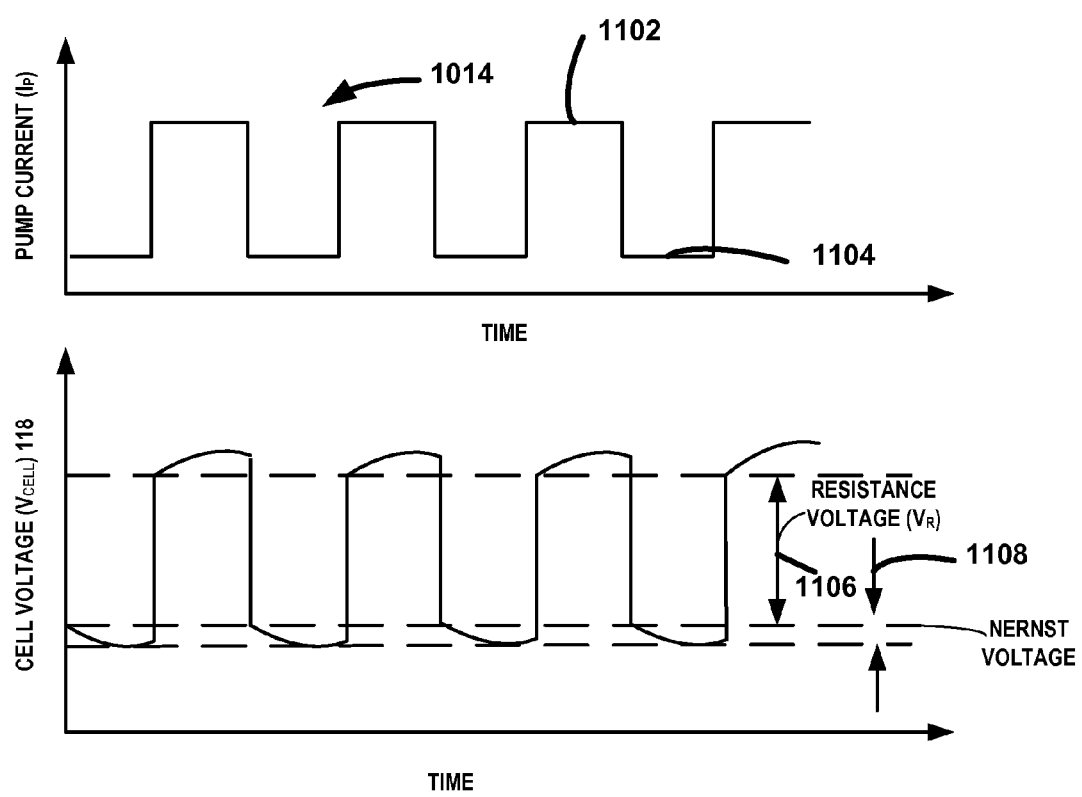
FIG. 11 is a graphical representation of an exemplary pump current and a corresponding cell voltage ($V_{CELL}$).

FIG. 11 is a graphical representation of an exemplary pump current 114 and a corresponding cell voltage ($V_{CELL}$) 1018. As the pump current 1014 is switched between a constant positive current 1102 and a constant negative current 1004, the voltage ($V_{CELL}$) across the electrochemical cell (pump cell) also oscillates between negative and positive voltage. As discussed above, a portion ($V_R$) 1106 of the total voltage ($V_{CELL}$) is due to the internal resistance (R) and is referred to as the resistance voltage ($V_R$) 1106. After the pump current is reversed, the opposite resistance voltage appears at the cell and begins to approach a threshold at the total cell voltage. The sum of the resistance voltage and the Nernst voltage 1108 is equal to the total cell voltage ($V_{CELL}$).

Figure 12:
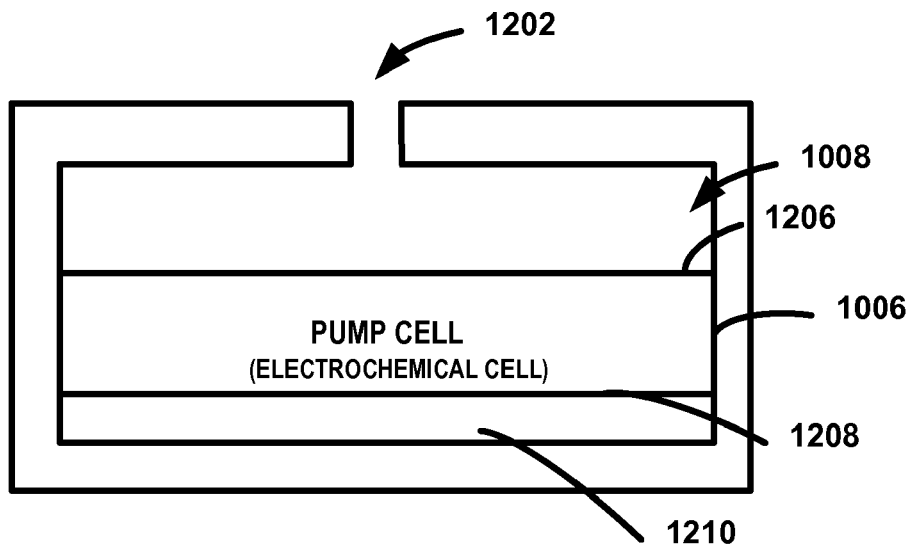
FIG. 12 is a block diagram of a cross sectional view of sensor including a single electrochemical cell and a diffusion gap for use as the measuring opening.

FIG. 12 is a block diagram of a cross sectional view of an exemplary sensor 1200 where the sensor 1200 includes a single electrochemical cell and a diffusion gap 1202 for use as the measuring opening 1010. A measuring side electrode is exposed to the measuring chamber 1008 and an atmospheric electrode is exposed to the atmospheric fluid 1210 such as air. As explained above, conventional wideband sensors exhibit a delay between Nernst reference cell output and changing pump cell current because of the physical separation between the two components. The delay is no longer applicable because the active electrode surface of the pump cell also reacts directly without delay on the measured gas. This will further increase the measurement speed. Accordingly, the embodiment illustrated in FIG. 12 provides an implementation exemplary implementation the wideband sensor is constructed without a separate sensor reference cell but otherwise in accordance with conventional techniques.

Figure 13:
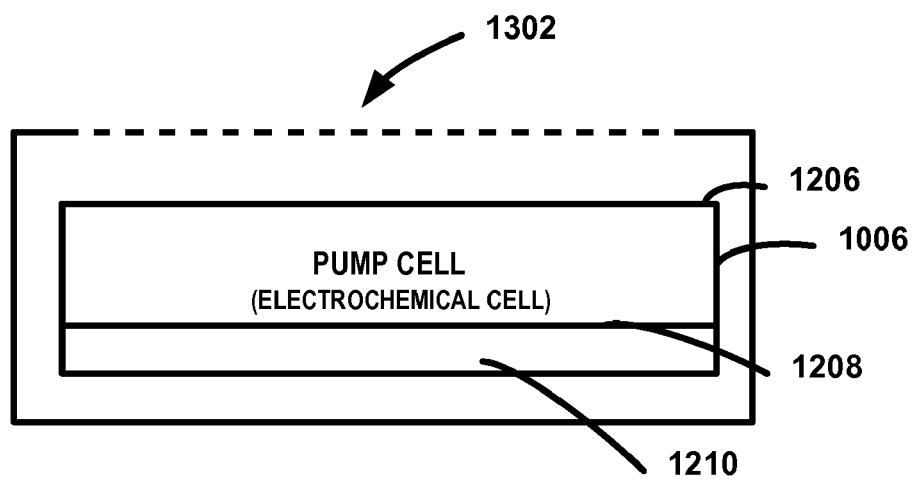
FIG. 13 is a block diagram of a cross sectional view of a sensor that includes a single electrochemical cell and a porous membrane for the measuring opening.

FIG. 13 is a block diagram of a cross sectional view of another exemplary sensor 1300 where the sensor 1300 includes a single electrochemical cell and a porous membrane 1302 for the measuring opening 1010. In the implementation shown in FIG. 13, measurement chamber and diffusion gap are omitted. The electrode of the pump cell that is exposed to exhaust gas is covered with an inert porous material that allows weak diffusion of exhaust gas to that sensor electrode. The single diffusion gap and measurement chamber of a conventional sensor is thus replaced with a multitude of diffusion channels. This essentially divides the pump cell surface into a multitude of parallel operating pump cells. This reduces greatly the chance that a single small particle covering the diffusion gap can render the sensor inoperable. Because each pump cell part also has to operate only on a much smaller gas sample compared to a regular wideband sensor, its operating speed can be further increased. The temperature of the sensor, which is important to measure because of its effects on diffusion speed and Nernst voltage can be measured via the internal resistance (Ohmish impedance) of the cell, as the material used for these sensors has a strong negative temperature coefficient. The porous layer may be made of a material that has strong thermal isolating characteristics. It can also serve as protection for the pump cell itself. With appropriate construction, this porous layer by itself can act as protection shield for the sensor, thus eliminating the slowdown in response speed caused by the flow dynamics of metallic shields around conventional wideband sensors.

Accordingly, the apparatus, system, and method discussed with reference to FIGS. 10-13 provides several advantages over conventional ion concentration measuring systems. The elimination of two devices provides more for more easily manufactured sensors and reduced delays within the sensors during use. More accurate results are obtained due to the PWM scheme as compared to control loop implementation. Since the internal resistance of the cell is temperature dependent the calculated internal resistance $R_{CELL}$ value can then be used to measure temperature and to regulate the temperature electrochemical cell (pump cell) by controlling the pump cell heater.

Clearly, other embodiments and modifications of this invention will occur readily to those of ordinary skill in the art in view of these teachings. Therefore, this invention is to be limited only by following claims, which include all such embodiments, equivalents, and modifications when viewed in conjunction with the above specification and accompanying drawings.

What is claimed is:

1. An apparatus comprising:
   an electrochemical cell for providing an output signal in accordance with an ion concentration within a measured fluid within a measuring cell and for adjusting an ion flow between the measuring cell and ambient fluid in accordance with a pump current flowing through the electrochemical cell, wherein the measuring cell has a fluid opening between the measuring cell and the ambient fluid; a current managing unit for varying the pump current between a first constant current and a second constant current in accordance with the output signal; and
   a computing device configured to determine the ion concentration based on a pulse width ratio of a square wave of the pump current.

2. An apparatus in accordance with claim 1, wherein the electrochemical cell comprises:
   an ion sensor cell for providing the output signal in accordance with the ion concentration within the measured fluid; and
   a pump cell for adjusting the ion flow between the measuring cell and ambient fluid in accordance with the pump current flowing through the pump cell.

3. An apparatus in accordance with claim 2, wherein the ion sensor cell is a gas ion sensor cell and the measured fluid is a measured gas.

4. An apparatus in accordance with claim 3, wherein the gas ion sensor cell is an oxygen sensor cell and the ambient fluid is ambient air.

5. An apparatus in accordance with claim 3, wherein the gas ion sensor cell is a nitrogen sensor cell responsive to gaseous oxides of nitrogen.

6. An apparatus in accordance with claim 2, wherein the current managing unit is configured to vary the pump current by maintaining the first constant current in a first direction until a first output signal threshold is detected and maintaining the second constant current in a second direction until a second output signal threshold is detected.

7. An apparatus in accordance with claim 6, wherein the current managing unit comprises:
   an analog comparator circuit configured to provide a comparator output signal based on the output of the ion sensor cell, the comparator output signal indicating when the first output signal threshold is reached and when the second output signal threshold is reached; and
   an inverting amplifier circuit connected between the analog comparator circuit and the ion sensor cell, the inverting amplifier circuit configured to change the direction of the pump current in response to the comparator output signal.

8. An apparatus in accordance with claim 7, wherein the computing device is configured to determine the pulse width ratio by:
- measuring a first time period corresponding to the first constant current;
- measuring a second time period corresponding to the second constant current;
- determining the pulse width ratio based on the first time period and the second time period; and
- determining the ion concentration by comparing the pulse width ratio to a pulse width ratio function for the measuring cell.

9. An apparatus in accordance with claim 8, wherein the computing device is connected to the comparator circuit, the computing device configured to measure the first time period and the second time period based on the comparator output signal.

10. An apparatus configured to connect to a measuring cell, the apparatus comprising:
- a current managing unit configured to receive an output signal based on an ion concentration within a measured fluid within the measuring cell and configured to adjust an ion flow between the measuring cell and ambient fluid by varying, in accordance with the output signal, a pump current flowing through a pump cell of the measuring cell between a first constant current and a second constant current, wherein the measuring cell has a fluid opening between the measuring cell and the ambient fluid; and
- a computing device configured to determine the ion concentration of the measured fluid based on a pulse width ratio of a square wave of the pump current.

11. An apparatus in accordance with claim 10, wherein the current managing unit is configured to vary the pump current by maintaining the first constant current in a first direction until a first output signal threshold is detected and maintaining the second constant current in a second direction until a second output signal threshold is detected.

12. An apparatus in accordance with claim 11, wherein the computing device is configured to determine the pulse width ratio by:
- measuring a first time period corresponding to the first constant current;
- measuring a second time period corresponding to the second constant current;
- determining the pulse width ratio based on the first time period and the second time period; and
- determining the ion concentration of the measured fluid by comparing the pulse width ratio to a pulse width ratio function for the measuring cell.

13. An apparatus in accordance with claim 10, wherein the output signal is produced by an ion sensor cell of the measuring cell.

14. An apparatus in accordance with claim 13, wherein the ion sensor cell is a gas ion sensor cell and the measured fluid is a gas.

15. An apparatus in accordance with claim 14, wherein the gas ion sensor cell is an oxygen sensor cell and the ambient fluid is ambient air.

16. An apparatus in accordance with claim 14, wherein the gas ion sensor cell is a nitrogen sensor cell responsive to gaseous oxides of nitrogen.

17. An apparatus comprising:
- a sensor connector configured to connect to a measuring cell and receive an output signal based on an ion concentration of a measured fluid within a measuring cell, wherein the measuring cell has a fluid opening between the measuring cell and ambient fluid;
- the output signal produced by an ion sensor cell of the measuring cell;
- a current managing unit configured to adjust an ion flow between the measuring cell and ambient fluid by varying, in accordance with the output signal, a pump current flowing through a pump cell of the measuring cell between a first constant current and a second constant current; and
- a computing device configured to determine the ion concentration of the fluid based on a pulse width ratio of a square wave of the pump current resulting from the varying of the pump current.

18. An apparatus in accordance with claim 17, wherein the current managing unit is configured to vary the pump current by maintaining the first constant current in a first direction until the output signal reaches a first output signal threshold and maintaining the second constant current in a second direction until the output signal reaches a second output signal threshold.

19. An apparatus in accordance with claim 18, wherein the ion sensor cell is a gas ion sensor cell and the measured fluid is a gas.

20. An apparatus in accordance with claim 19, wherein the gas ion sensor cell is an oxygen sensor cell and the ambient fluid is ambient air.

21. An apparatus in accordance with claim 19, wherein the gas ion sensor cell is a nitrogen sensor cell responsive to gaseous oxides of nitrogen.

22. An ion concentration measuring system comprising:
- a sensor comprising:
  - a measuring chamber having an ambient opening configured to receive an ambient fluid and a measuring opening configured to receive a measured fluid; and
  - an electrochemical cell configured to change an ion concentration within the measuring chamber in accordance with a pump current flowing through the electrochemical cell and configured to present a cell voltage in accordance with the ion concentration; and
- a sensor measuring device configured to vary the pump current between a first constant current and a second constant current in accordance with the cell voltage, wherein the sensor measuring device comprises a computing device configured to calculate the ion concentration of the fluid based on the cell voltage.

* * * * *